(12) United States Patent
Deslauriers et al.

(10) Patent No.: US 8,668,697 B2
(45) Date of Patent: Mar. 11, 2014

(54) METHODS AND DEVICES FOR STERNAL CLOSURE

(75) Inventors: Richard J. Deslauriers, Woodbury, CT (US); Eric Kolb, Sandy Hook, CT (US)

(73) Assignee: ABYRX, Inc., Irvington, NY (US)

(*) Notice: Subject to any disclaimer, the term of this patent is extended or adjusted under 35 U.S.C. 154(b) by 564 days.

(21) Appl. No.: 12/862,191

(22) Filed: Aug. 24, 2010

(65) Prior Publication Data

US 2011/0082497 A1    Apr. 7, 2011

Related U.S. Application Data

(63) Continuation-in-part of application No. 12/575,060, filed on Oct. 7, 2009, now Pat. No. 8,337,497.

(51) Int. Cl.
| | |
|---|---|
| *A61B 17/56* | (2006.01) |
| *A61B 17/58* | (2006.01) |
| *A61B 17/82* | (2006.01) |
| *A61F 2/30* | (2006.01) |

(52) U.S. Cl.
USPC ............................................. 606/74; 606/282

(58) Field of Classification Search
USPC .............................. 606/280, 70, 71, 281, 282
See application file for complete search history.

(56) References Cited

U.S. PATENT DOCUMENTS

| | | |
|---|---|---|
| 3,030,951 A | 4/1962 | Mandarino |
| 3,112,743 A | 12/1963 | Cochran et al. |
| 3,802,438 A | 4/1974 | Wolvek |
| 3,945,376 A | 3/1976 | Kuehnegger |
| 4,201,215 A | 5/1980 | Crossett et al. |
| 4,279,248 A | 7/1981 | Gabbay |
| 4,458,365 A | 7/1984 | Wood |
| 4,512,346 A | 4/1985 | Lemole |
| 4,593,541 A | 6/1986 | Hollis |
| 4,730,615 A | 3/1988 | Sutherland et al. |
| 4,735,206 A | 4/1988 | Hewson |
| 4,813,416 A | 3/1989 | Pollak et al. |
| 4,944,753 A | 7/1990 | Burgess et al. |

(Continued)

FOREIGN PATENT DOCUMENTS

WO    2006/060911 A1    6/2006

OTHER PUBLICATIONS

Robert Selthofer et al., "Morphometric Analysis of the Sternum" as published in Coll. Antropol. 30 (2006) 1:43-47.

(Continued)

*Primary Examiner* — Andrew Yang
(74) *Attorney, Agent, or Firm* — Ivor R. Elrifi; Muriel Liberto, Esq.; Mintz Levin Cohn Ferris Glovsky and Popeo, P.C.

(57) ABSTRACT

A method for closing a sternum separated into at least a first sternum portion and a second sternum portion includes preparing at least one cut surface of at least one of the first or second sternum portions to have an adhesive applied thereon. The adhesive is applied to at least a portion of the at least one cut surface. The at least one cut surface is approximated to a second cut surface of the other of the first sternum portion or second sternum portion. As the adhesive cures, it bonds with the first cut surface and the second cut surface. Preparing the at least one cut surface may remove contaminants that could inhibit adhesion of the adhesive. The adhesive may be applied through adhesive injection holes formed along an incision separating the first and second sternum portions. Devices for preparing the cut surfaces and applying the adhesive are also provided.

13 Claims, 17 Drawing Sheets

(56) References Cited

U.S. PATENT DOCUMENTS

| | | |
|---|---|---|
| 5,163,598 A | 11/1992 | Peters et al. |
| 5,356,417 A | 10/1994 | Golds |
| 5,417,698 A | 5/1995 | Green et al. |
| 5,462,542 A | 10/1995 | Alesi, Jr. |
| 5,514,137 A | 5/1996 | Coutts |
| 5,626,618 A | 5/1997 | Ward et al. |
| 6,007,538 A | 12/1999 | Levin |
| 6,051,007 A | 4/2000 | Hogendijk et al. |
| 6,358,270 B1 | 3/2002 | Lemer |
| 6,368,342 B1 | 4/2002 | Lemer |
| 6,540,769 B1 | 4/2003 | Miller, III |
| 6,712,821 B2 | 3/2004 | Gabbay |
| 6,858,016 B2 | 2/2005 | Davaris et al. |
| 6,969,398 B2 | 11/2005 | Stevens et al. |
| 7,011,628 B2 | 3/2006 | LiDonnici |
| 7,252,841 B2 | 8/2007 | Constantz et al. |
| 7,361,179 B2 | 4/2008 | Rousseau et al. |
| 7,482,504 B2 | 1/2009 | Brothers |
| 2005/0220771 A1 | 10/2005 | Deslauriers et al. |
| 2007/0218144 A1 | 9/2007 | Lally |
| 2010/0179600 A1 | 7/2010 | Steger et al. |

OTHER PUBLICATIONS

A.R. Casha et al., "A Biomechanical Study of Median Sternotomy Closure Techniques" as published in European Journal of Cardiothoracic Surgery 15 (1999), pp. 365-369.

Search Report and Written Opinion from corresponding International Appln. No. PCT/US2011/043502 dated Mar. 14, 2012 (11 pages).

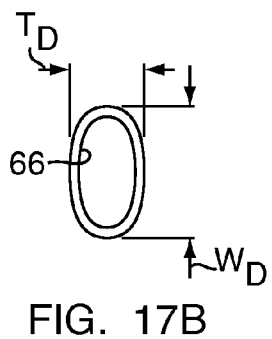 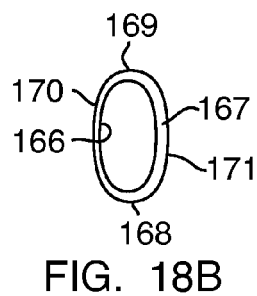 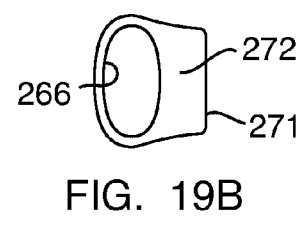
FIG. 17B    FIG. 18B    FIG. 19B
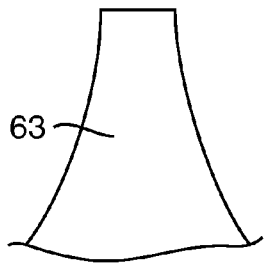 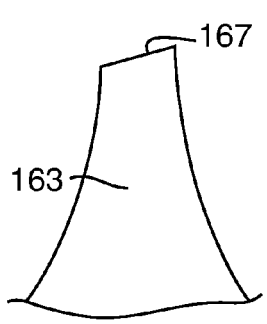 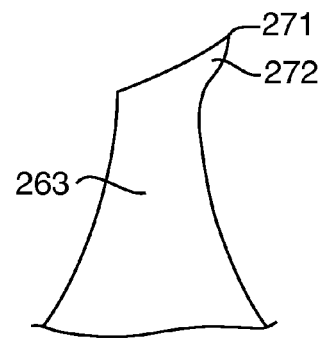
FIG. 17C    FIG. 18C    FIG. 19C
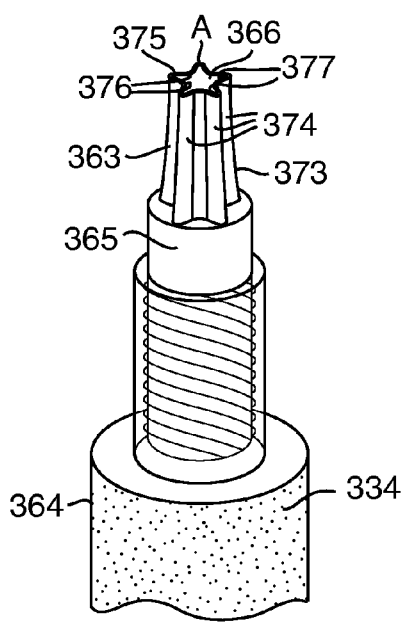 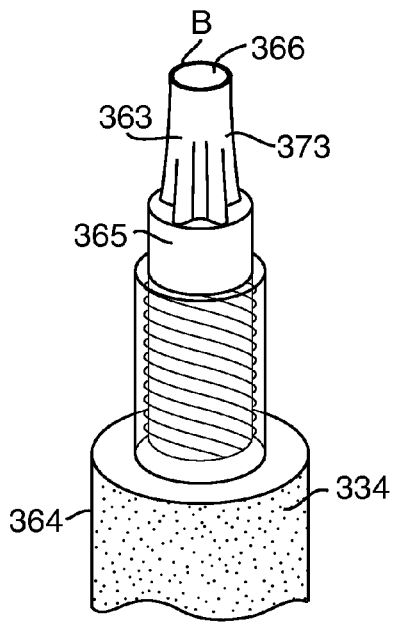
FIG. 20A    FIG. 20B

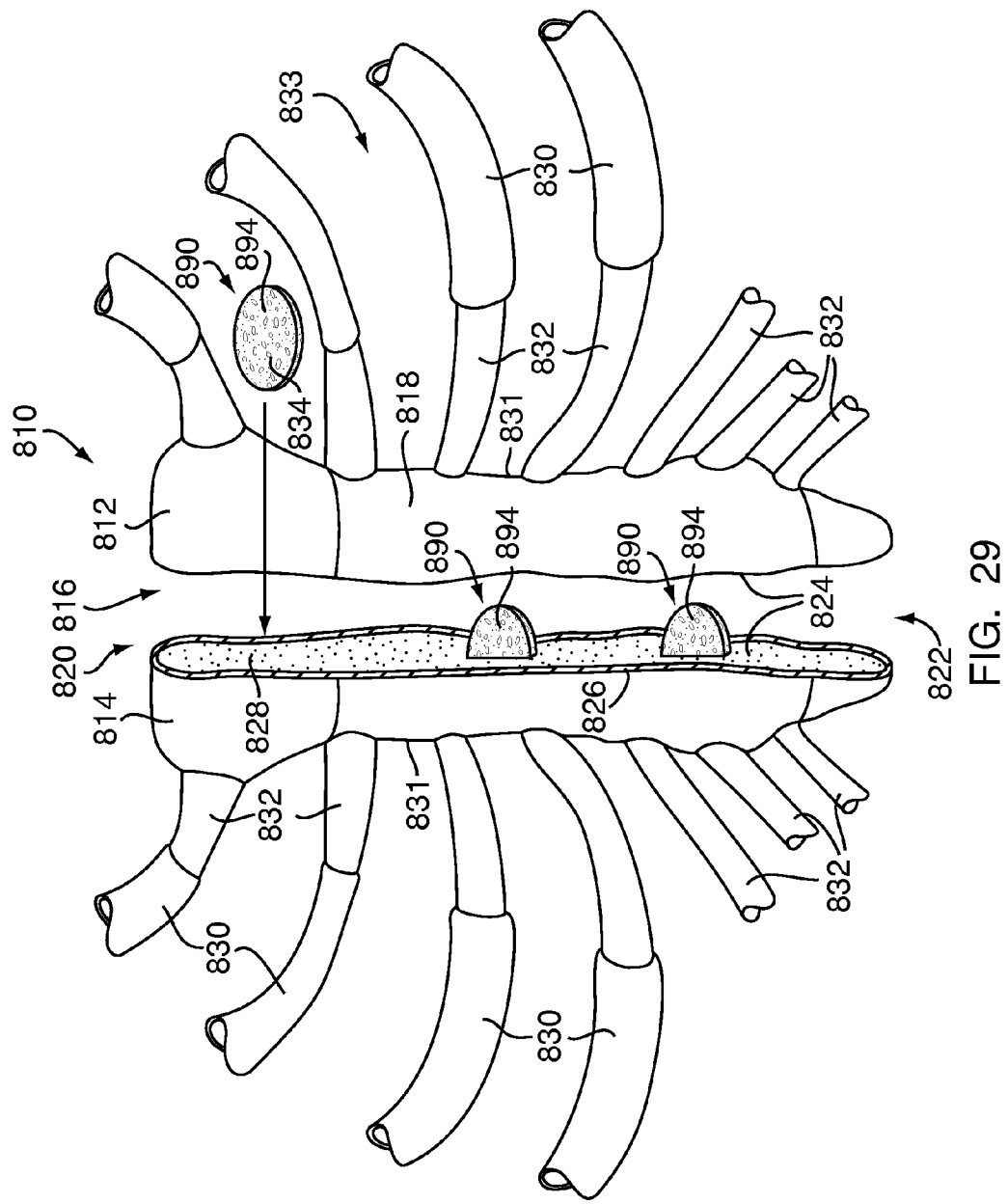

METHODS AND DEVICES FOR STERNAL CLOSURE

CROSS REFERENCE TO RELATED APPLICATIONS

This application is a continuation-in-part of U.S. patent application Ser. No. 12/575,060, filed Oct. 7, 2009, which is hereby incorporated by reference in its entirety.

FIELD OF THE INVENTION

The present invention relates to surgical procedures and, more particularly, to sternal surgical procedures.

BACKGROUND OF THE INVENTION

During surgical procedures, an incision is made to provide a surgeon with access to a patient's internal organs. At the end of the surgical procedure, the incision is closed to the external environment, thereby allowing the patient to heal and recover from the surgery. For surgical procedures to organs within a patient's thoracic cage, such as the heart and lungs, the patient's sternum may need to be separated to provide the surgeon with access to the organs.

The sternum is an elongated, generally flat, bone located longitudinally in the center of the thorax. The sternum has a composite bone structure with a dense outer shell formed from cortical bone surrounding a low density core formed from cancellous bone. The sides of the sternum are connected to rib bones through cartilage to form the anterior section of the thoracic cage, which protects the lungs, heart and other organs from physical trauma.

A sternotomy is a surgical procedure in which a midline longitudinal incision is made through at least a portion of the sternum to allow the opposing portions to be separated to provide access to organs within the thoracic cage. The sternotomy may be median, whereby the midline incision is made over the entire longitudinal length of the sternum. Alternatively, the sternotomy may be a less invasive partial sternotomy or hemi sternotomy, whereby the midline longitudinal incision is made over only a portion of the length of the sternum along with one or more transverse incisions from a peripheral edge of the sternum to the midline incision, which allow a relatively small portion of the sternum to be separated. When the surgical procedure is complete, the separated opposing portions of the sternum are approximated to one another to close the incision and secured to one another so that the incision may heal.

Conventional closure devices for approximating and closing sternal incisions include wires, cables or bands that generally wrap around the sternum between the ribs to provide a compressive load across the sternal incision. While these conventional devices restrain the sternum portions from pulling apart, they do little to resist other forms of relative motion, for example, sliding of one cut surface relative to the other or flexing motion about the incision. These non-prevented relative movements may result in pain and discomfort for the patient, as well as more severe complications such as infections, all of which may lead to prolonged medication, decreased lung capacity and a longer return to normal functionality (e.g. a return to work). Additionally, the relative movement may cause soft fibrous scar tissue to form across the incision, rather than the desired bone growth. The fibrous scar tissue must be subsequently removed with further surgical procedures.

Relative motion between the two sternal portions may also cause the conventional devices to loosen. For example, in the case of devices secured by twisted wire, the wire may untwist. More severely, the relative motion may cause the conventional devices to cut into and pull through the sternum bone, which also results in a loosening of the devices and separation of the sternal portions. This separation may delay healing or may result in additional surgical procedures to tighten or replace the conventional closure devices. The loosening or pulling through of the conventional devices may be caused by loading that the patient cannot practically control, such as cyclic loading due to normal respiration as well as less frequent high cycle loads generated during coughing or sneezing.

Another conventional closure device includes a metal plate that is fastened to an anterior surface of the sternum. While the metal plate inhibits relative movement between the two sternal portions better than conventional wires and cables, the metal plate has its own limitations and disadvantages. For instance, the thickness of metal plate closure devices results in discomfort to the patient. Additionally, the relative movement between the sternal portions may result in a failed screw purchase. With a failed screw purchase, one or more of the screws fastening the metal plate to the sternum strips the sternum bone, allowing the screw or screws to pull out of the bone. The loose screw or screws allow the metal plate to loosen from the sternum causing pain and discomfort for the patient. Furthermore, metal plate closure devices are costly and difficult to remove in the event there is a need for future access to the thoracic cavity.

Accordingly, there is a need for an improved method for sternal closure that overcomes the deficiencies of the prior art.

SUMMARY OF THE INVENTION

According to the present invention, a method for closing a sternum separated into at least a first sternum portion and a second sternum portion includes preparing at least one cut surface of at least one of the first sternum portion or second sternum portion to have an adhesive applied thereon. The adhesive is applied to at least a portion of the at least one cut surface and the at least one cut surface is approximated to a second cut surface of the other of the first sternum portion or second sternum portion. As the adhesive cures, it bonds with the first cut surface and the second cut surface. Preparing the at least one cut surface may advantageously remove contaminants that could inhibit adhesion of the adhesive.

In some embodiments, the at least one cut surface may be prepared using a lavage system. In these embodiments, sensitive organs may be protected from contact with pressurized cleaning fluid from the lavage system. The cleaning fluid and contaminants may also be vacuumed from the at least one cut surface. In some embodiments, the adhesive may be applied to the cut surface through a nozzle of the lavage system.

According to the present invention, a nozzle for use with the lavage system includes an elongated body having a first end adapted to connect to the lavage system and a second end having a protective blade connected thereto. The nozzle includes at least one fluid channel extending through the elongated body from the first end to an outlet above the protective blade. The nozzle may also include a second fluid passage extending through the elongated nozzle body from the first end to a port above the protective blade. The second fluid passage may be connected to an adhesive delivery system or to a vacuum system. In some embodiments, the nozzle may also include a top blade connected to the elongated nozzle body above the outlet.

According to some embodiments of the present invention, the at least one cut surface may be prepared using a brush having an elongated body with a handle disposed at one end thereof and a brush head disposed at the other end. The brush head may include bristles for preparing the at least one cut surface. In some embodiments, the bristles may have a hemostatic chemical agent disposed thereon. The bristles may be divided into a central portion having substantially soft bristles and two outer portions having more rigid bristles than the central portion. In some embodiments, the bristles of the outer portions may be substantially perpendicular to the bristles of the central portion.

According to some embodiments of the present invention, the adhesive may be applied to substantially the entire cut surface in a single pass of an adhesive applicator. The adhesive applicator may also push the adhesive into cancellous bone of the at least one cut surface. Preferably, the adhesive applicator includes a dispenser outlet of a non-circular shape to apply a thin broad strip of adhesive to the at least one cut surface. The adhesive applicator may also include a bevel at the dispenser outlet to facilitate application of the adhesive at an angle. In some embodiments, the adhesive may be applied to only the cancellous bone of the at least one cut surface.

In some embodiments, the adhesive applicator may include a resilient sidewall that may deform to change a cross-sectional area of the dispenser outlet. The resilient sidewall may include a plurality of waves having crests and troughs extending longitudinally from a base of the adhesive applicator to the dispenser outlet.

According to the present invention, a method for closing a sternum separated by an incision into at least a first sternum portion and a second sternum portion includes bringing the first sternum portion and second sternum portion into contact at the incision and fastening the first sternum portion to the second sternum portion. Adhesive injection holes are formed along the incision and adhesive is injected therein. The first and second sternum portions may be fastened with wires. In some embodiments, the adhesive injection holes may be expanded by compressing cancellous bone of the first sternum portion and the second sternum portion. The cancellous bone may be compressed by inflating a balloon within the adhesive injection holes to compress the cancellous bone.

These and other objects, features and advantages of the present invention will become apparent in light of the following detailed description of non-limiting embodiments, with reference to the accompanying drawings.

BRIEF DESCRIPTION OF THE DRAWINGS

FIG. 17B is top view of an adhesive applicator tip of the adhesive application device of FIG. 17A;

FIG. 17C is a partial side view of the adhesive applicator tip of the adhesive application device FIG. 17A;

FIG. 18B is top view of an adhesive applicator tip of the adhesive application device of FIG. 18A;

FIG. 18C is a partial side view of the adhesive applicator tip of the adhesive application device FIG. 18A;

FIG. 19B is top view of an adhesive applicator tip of the adhesive application device of FIG. 19A;

FIG. 19C is a partial side view of the adhesive applicator tip of the adhesive application device FIG. 19A;

FIG. 20A is a side perspective view of a further embodiment of an adhesive applicator tip according to the present invention;

FIG. 20B is a side perspective view of the adhesive applicator tip of FIG. 20A under a relatively high pressure;

FIG. 29 is a perspective of the separated sternum of FIG. 1 with structural member placed therein in accordance with another embodiment of the present invention;

DETAILED DESCRIPTION OF A PREFERRED EMBODIMENT

Figure 1:
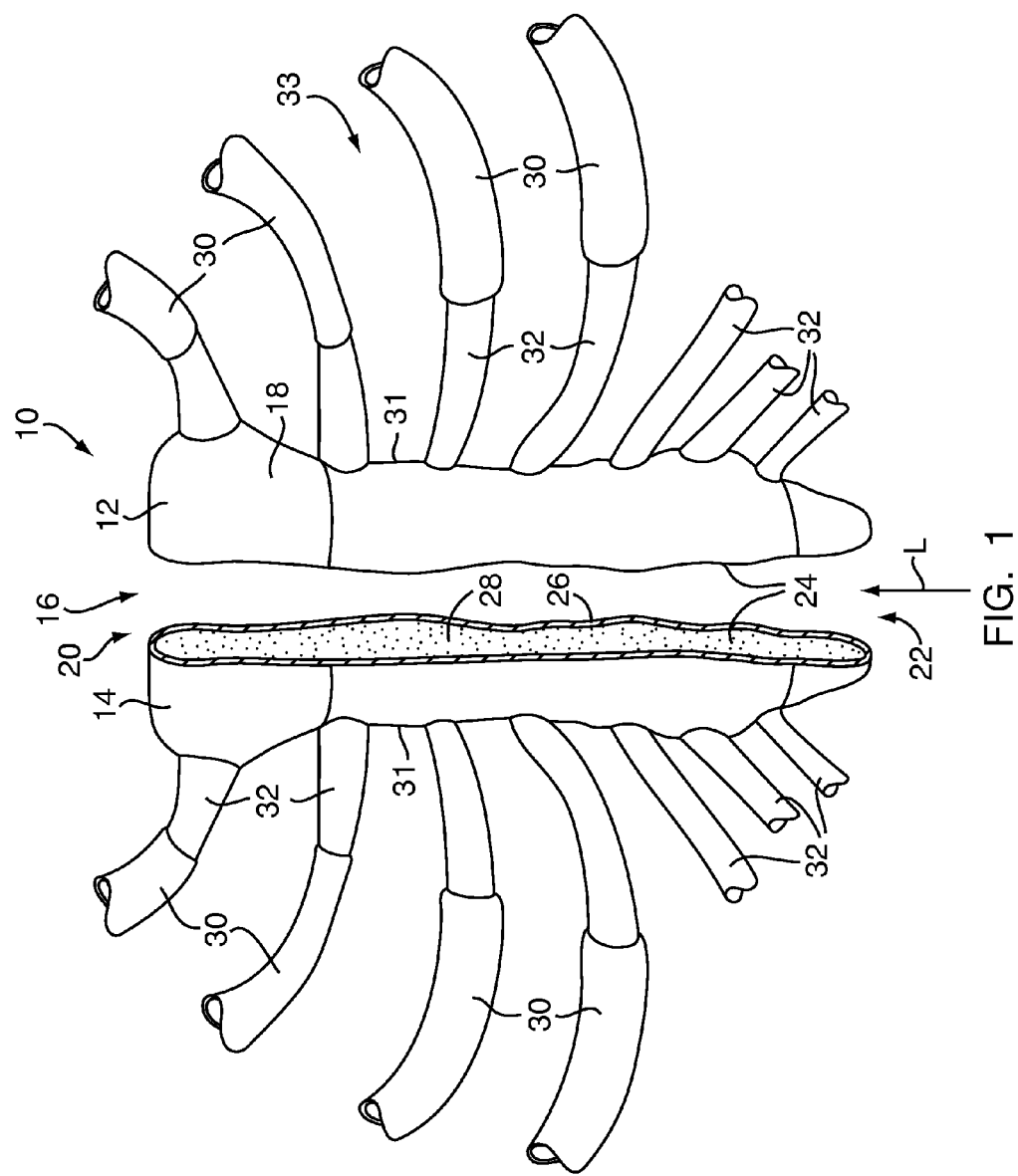
FIG. 1 is a perspective view of a separated sternum.

Referring to FIG. 1, the present invention provides a method for closure of a sternum 10 that has been separated into a first sternum portion 12 and a second sternum portion 14 by an incision 16, for example, from a surgical procedure such as a median sternotomy. The incision 16 extends in a longitudinal direction L approximately along a midline of the anterior surface 18 of the sternum 10 from an upper end 20 to a lower end 22. The incision 16 forms a cut surface 24 on each of the first and second sternum portions 12 and 14, exposing the sternum's composite bone structure having a shell of cortical bone 26 surrounding a core of cancellous bone 28. A plurality of rib bones 30 are connected to peripheral edges 31 of the sternum 10 by cartilage 32 to form a thoracic cage 33 for protecting internal organs from physical trauma.

Figure 2:
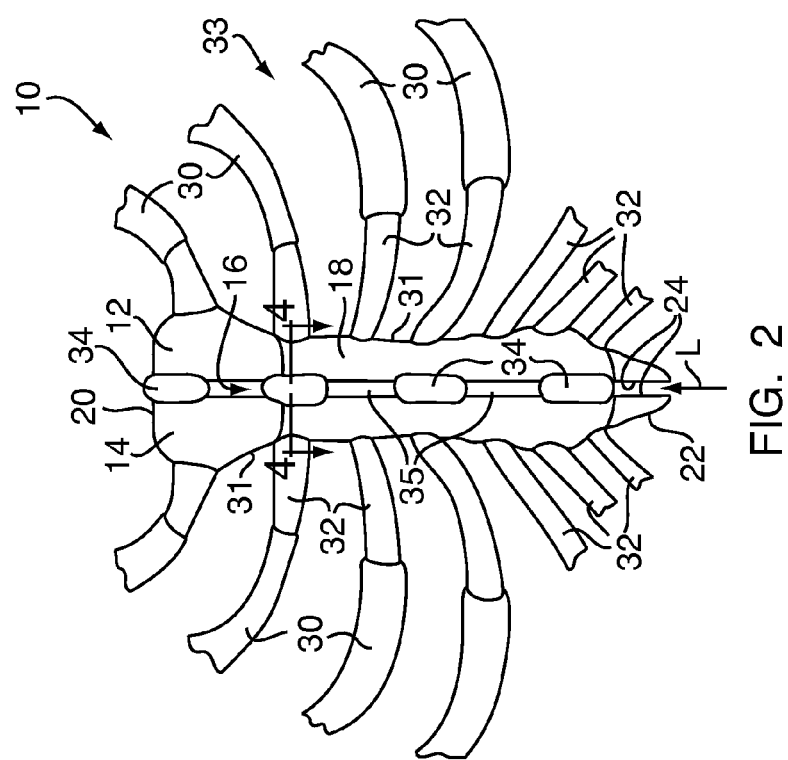
FIG. 2 is a front view of the separated sternum of FIG. 1 with adhesive placed therein in accordance with an embodiment of the present invention.

Referring to FIG. 2, at the end of the surgical procedure, such as a sternotomy, an adhesive 34 is applied to the at least one of the first and second sternum portions 12 and 14 and the first and second sternum portions 12 and 14 are brought proximate to one another. Preferably, the adhesive 34 is applied as a liquid or taffy-like material, as will be discussed in more detail below. When the sternum portions 12 and 14 are brought together, the adhesive 34 on one sternum portion, for example, the first sternum portion 12, contacts the opposing cut surface 24 of, for example, the second sternum portion 14. Thus, the incision 16 between the first and second sternum portions 12 and 14 becomes partially filled with the adhesive 34. The adhesive 34 is applied so that it is located at a plurality of longitudinal locations along the incision 16 interrupted by gaps 35 between each instance of adhesive 34. Preferably, the adhesive 34 covers approximately twenty percent (20%) to approximately eighty percent (80%) of the longitudinal length of the incision 16 and, even more preferably, covers approximately thirty percent (30%) to approximately seventy percent (70%) of the longitudinal length of the incision 16.

Figure 3:
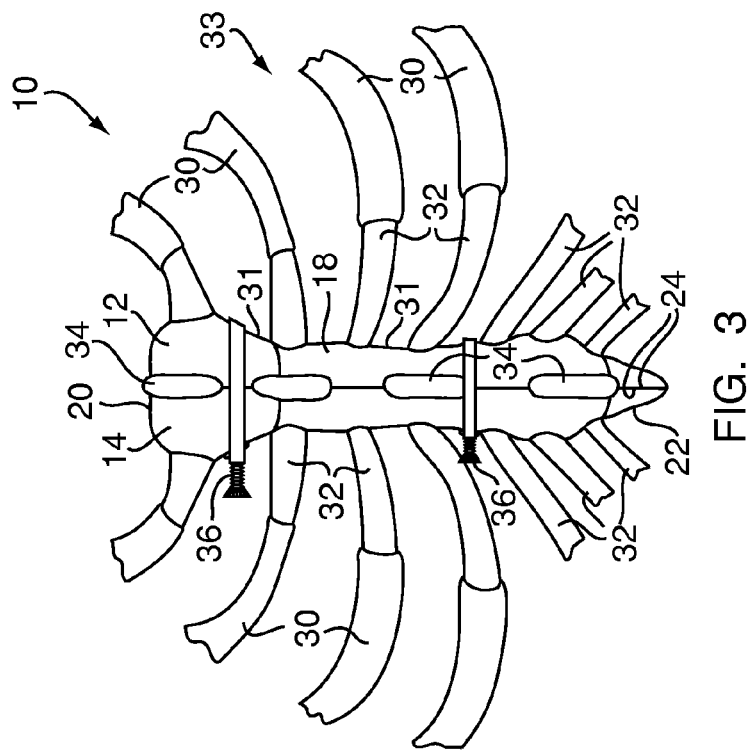
FIG. 3 is a front view of the separated sternum of FIG. 2 with first and second sternum portions compressed.

Once the adhesive 34 has been applied to the sternum 10 within incision 16, the first and second sternum portions 12 and 14 may be maintained proximate to one another until the adhesive 34 has bonded with each of the first and second sternum portions 12 and 14. More preferably, as seen in FIG. 3, the first and second sternum portions 12 and 14 are compressed together, with the cut surfaces 24 abutting one another. The first and second sternum portions 12 and 14 may be permanently compressed, as will be discussed in more detail below, or the first and second sternum portions 12 and 14 may be temporarily compressed through the use of clamps 36 or other known compressive devices. Compressing the first and second sternum portions 12 and 14 together forces some of the adhesive 34 into the porous structure of the internal cancellous bone 28, thereby increasing the bond formed when the adhesive polymerizes, as will be discussed in more detail below. The clamps 36 are then removed once the adhesive 34 has cured.

Figure 4:
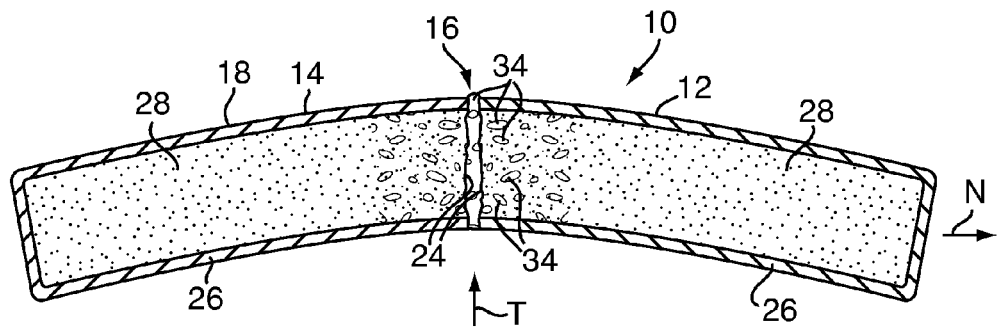
FIG. 4 is a cross-sectional view of the separated sternum with adhesive placed therein of FIG. 2.

Referring to FIG. 4, the adhesive 34 may be applied to the cut surfaces 24 within incision 16 over substantially the entire thickness of the sternum 10 to maximize contact with the sternum portions 12 and 14 and to provide a strong bond between the first and second sternum portions 12 and 14. Additionally, applying the adhesive 34 to substantially the entire thickness of the cut surface 24 allows the adhesive 34 to bond with both the cortical bone 26 and the cancellous bone 28 of the first and second sternum portions 12 and 14.

The bond formed by adhesive 34 between the first and second sternum portions 12 and 14 is preferably both chemical, due to adhesive properties of the adhesive 34, and mechanical, due to a portion of the adhesive 34 partially invading or infiltrating the porous structure of the cancellous bone 28 and/or cortical bone 26 of the sternum 10. Additionally, the adhesive 34 preferably has expansion characteristics that facilitate the bonding of the adhesive 34 to the first and second sternum portions 12 and 14. For example, once the adhesive 34 has been applied to the first and second sternum portions 12 and 14 and the portions have been brought proximate to one another, the adhesive 34 may expand into the porous structure of the cancellous bone 28. Once the first and second sternum portions 12 and 14 have been approximated, the cortical bone 26 acts as a seal to guide the expanding adhesive 34 into the cancellous bone 28. Preferably, the adhesive expands into the cancellous bone 28 of the first and second sternum portions 12 and 14 in the range of approximately 1 mm to approximately 10 mm. The adhesive 34 then polymerizes within the porous structure of the cancellous bone 28 to provide a strong mechanical bond between the first and second sternum portions 12 and 14.

The bonded adhesive 34 resists relative motion between the first and second sternum portions 12 and 14 and holds the incision 16 closed to allow bone growth between the first and second sternum portions 12 and 14 so that the patient may heal after the surgical procedure. In particular, the bonded adhesive 34 prevents the first and second sternum portions 12 and 14 from shearing with one another in the longitudinal direction L, shown in FIG. 2, from flexing about the incision 16 due to loads in the transverse direction T, shown in FIG. 4, and from separating in a normal direction N, normal to the cut surfaces 24, as shown in FIG. 4. Thus, the bond provided by adhesive 34 prevents shearing, flexing and separation of the first sternum portion 12 from the second sternum portion 14 due to loads from intentional musculoskeletal movement, unintentional loading (i.e. physical trauma) as well as cyclical loads caused by breathing, sneezing, coughing or the like.

The adhesive 34 is preferably a biocompatible polymeric adhesive material, which is osteoconductive and promotes bone growth when used in medical procedures. Suitable biocompatible polymeric adhesive material for the present invention may be formed from a polyurethane/polyurea such as the KRYPTONITE™ bone matrix product, available from DOCTORS RESEARCH GROUP, INC. of Southbury, Conn., and also described in U.S. patent application Ser. No. 11/089,489, which is hereby incorporated by reference in its entirety.

The biocompatible polymeric material may combine an isocyanate with one or more polyols and/or polyamines, along with optional additives (e.g., water, filler materials, catalysts, surfactants, proteins, and the like), permitting the materials to react to form a composition that comprises biocompatible polyurethane/polyurea components. As referred to herein, the term "biocompatible polyurethane/polyurea components" includes, inter alia, biocompatible polyester urethanes, biocompatible polyether urethanes, biocompatible poly(urethane-ureas), biocompatible polyureas, and the like, and mixtures thereof.

Certain embodiments may comprise biocompatible polyurethane/polyurea components present in an amount in the range of from about twenty percent to about ninety percent (20% to about 90%) by weight of the composition, with the balance comprising additives. Certain embodiments of the compositions made according to the present invention may comprise biocompatible polyurethane/polyurea components present in an amount in the range of from about fifty percent to about eighty percent (50% to about 80%) by weight of the composition, with the balance comprising additives.

The biocompatible polymeric material is initially prepared in a liquid state, which is chemically adhesive. As the biocompatible polymeric material cures, it will pass through a taffy-like state, during which it is highly chemically adhesive. The biocompatible polymeric material then passes into a putty-like state in which the material's adhesive properties are reduced and the material is easily malleable and may be shaped and sculpted. The biocompatible polymeric material then cures into a final solid state. Since the adhesive properties of the biocompatible polymeric material are greatest when the material is in the liquid or taffy-like state, the material is preferably in either the liquid state or the taffy-like state when applied as adhesive 34. In the final solid state, the biocompatible polymeric material has a porous structure that promotes bone growth and is able to be cut in a similar manner to bone with a sternal saw. Thus, when used in sternal closure procedures according to the present invention, quick access to the thoracic cavity may be gained in the event that future surgical procedures are necessary.

Referring back to FIG. 2, as discussed above, in one embodiment, the adhesive 34 is applied intermittently along the incision 16 to provide the bond between the first and second sternum portions 12 and 14. The gaps 35 formed between the instances of adhesive 34 provide direct bone to bone contact between the first and second sternum portions 12 and 14, when compressed, which allows for direct bone growth between the first and second sternum portions 12 and 14 as the patient heals, thereby promoting natural healing after the surgical procedure. Preferably, the adhesive 34 has a porous structure and has osteoconductive properties so that bone growth also occurs between the first and second sternum portions 12 and 14 through the adhesive as the patient heals. The combination of the adhesive's mechanical strength, adhesiveness and porous structure makes the adhesive 34 unique in its utility as a sternal closure material.

For example, the peak load across the incision 16 of the sternum 10 due to coughing is approximately 1500N as taught by the article entitled "A Biomechanical Study of Median Sternotomy Closure Techniques" by A. R. Casha et al. as published in the European Journal of Cardio-thoracic Surgery 15 (1999) 365-369, which is hereby incorporated by reference in its entirety. The load that the adhesive 34 is capable of supporting can be calculated using the equation:

$$\text{LOAD} = S \times A,$$

where,

S is the strength of the material used for the adhesive 34; and

A is the surface area of the cut surface 24 coated with adhesive 34.

The KRYPTONITE™ bone matrix product, which is suitable as the adhesive 34 as discussed above, has a fatigue strength of approximately 2 MPa (as tested per ASTM F2118). The surface area of each cut surface 24 will vary patient to patient, but there average cross sectional area is approximately 14.5 cm(2) women and approximately 17.0 cm(2) for men, as calculated from data provided in the article entitled "Morphometric Analysis of the Sternum" by Robert Selthofer et al. as published in Coll. Antropol. 30 (2006) 1: 43-47, which is hereby incorporated by reference in its entirety. Thus, the load that the KRYPTONITE™ bone matrix product can support if the entire cut surface 24 is coated can be approximately 2900N for women and approximately 3500N for men, which is over two times the approximate peak load of 1500N. Therefore, applying the adhesive 34 to approximately half of the cut surfaces 24 in intervals, as discussed above, will provide sufficient strength to bond the first and second sternum portions 12 and 14 together, while allowing the other half of the cut surfaces 24 to contact each other to facilitate bone growth. As should be understood by those skilled in the art, there may be a large variation in the peak load value and the surface area of the cut surfaces 24 depending upon the patient's age, size, fitness and various other factors.

Although described as applying the adhesive 34 prior to approximating the first and second sternum portions 12 and 14, the method for sternal closure may instead apply the adhesive 34 to one or both of the cut surfaces 24 within the incision 16 after bringing the first and second sternum portions 12 and 14 proximate to one another.

Preferably, the cut surfaces 24 are prepared for the adhesive 34 prior to application of the adhesive 34 to remove surface contaminants that may affect adhesion and/or to expose the bone porosity to improve the mechanical bond provided by the adhesive 34. For instance, the cut surfaces 24 may be treated to remove, bone fragments, fat, blood, fluids, soft tissues or any other material that could affect adhesion between the cut surfaces 24.

Figure 5:
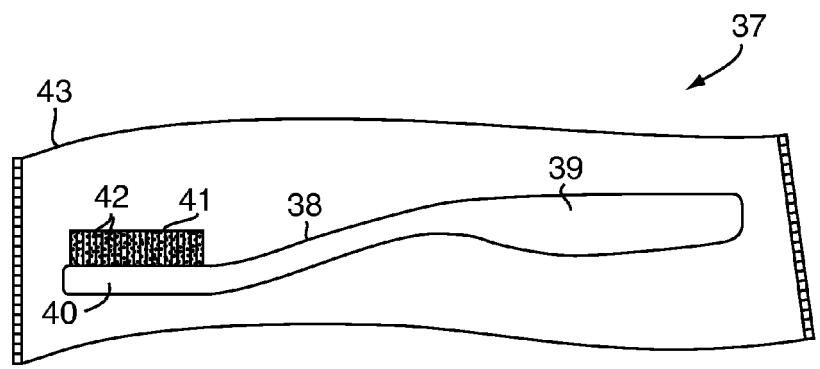
FIG. 5 is a side view of an embodiment of a cleaning brush according to the present invention.

Referring to FIG. 5, in some embodiments, a cleaning brush 37 may be provided for treating the cut surfaces 24, shown in FIG. 1. The cleaning brush 37 includes an elongated body portion 38 extending outwardly from a handle portion 39 to a brush head 40. The elongated body portion 38 has bristles 41 disposed on the brush head 40 for treating the cut surfaces 24, shown in FIG. 1. The bristles 41 may have a hemostatic chemical agent 42 disposed thereon. The hemostatic chemical agent 42 may be, for example, a hemostatic polymer powder such as that sold by Medafor, Inc. of Minneapolis, Minn. In some embodiments, the cleaning brush 37 with the hemostatic chemical agent 42 disposed on bristles 41 may be pre-packed in a sterile packaging 43 so that the cleaning brush 37 is ready for use upon removal from the sterile packaging 43. In other embodiments, the hemostatic chemical agent 42 may be provided separately within the same sternal closure kit so that a surgeon may apply the hemostatic chemical agent 42 to the bristles 41 or directly to the cut surface 24, shown in FIG. 1, prior to treating the cut surfaces 24, shown in FIG. 1. In operation, the surgeon may remove the cleaning brush 37 from the sterile packaging 43 and apply the hemostatic chemical agent 42 to the bristles 41, if not pre-packaged thereon. The surgeon may then hold the cleaning brush 37 by the handle portion 39 and brush the cut surfaces 24, shown in FIG. 1, with the bristles 41. The bristles 41 will remove contaminants that could affect adhesion from the cut surfaces 24, shown in FIG. 1, while the hemostatic chemical agent 42 advantageously controls bleeding.

Figure 6:
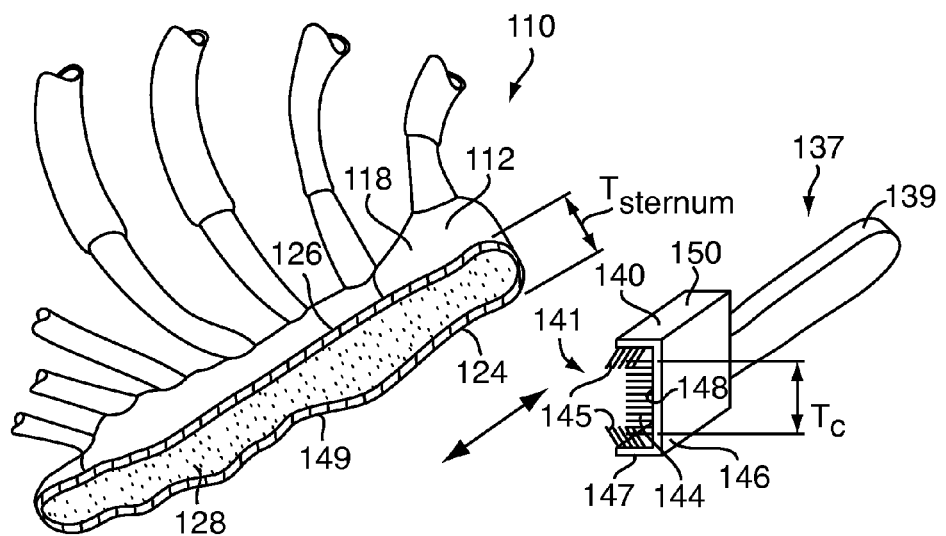
FIG. 6 is a front perspective view of another embodiment of a cleaning brush according to the present invention.

Referring to FIG. 6, wherein like numerals represent like elements, in some embodiments, the cleaning brush 137 may include brush head 140 having bristles 141 divided into a central portion 144 that is flanked on either side by an outer portion 145. Preferably, the central portion 144 has a central portion thickness $T_C$ that is approximately equal to a sternum thickness $T_{Sternum}$ of the sternum 110. In this embodiment, the brush head 140 may include a central base portion 146 flanked on each side thereof by substantially perpendicular outer base portions 147 to form a cleaning channel 148. The central portion 144 of the bristles 141 is disposed within the cleaning channel 148 on the central base portion 146 and each outer portion 145 of the bristles 141 is disposed within the cleaning channel 148 on each outer base portion 147. In some embodiments, the bristles 141 of each outer portion 145 may be substantially perpendicular to the bristles 141 of the central portion 144, while in other embodiments, the bristles 141 of each outer portion 145 may be angled away from the central portion 144. The bristles 141 within the central portion 144 are preferably relatively soft compared to the bristles 141 within each outer portion 145. The bristles 141 of the outer portions 145 may be formed from a rigid polymer or metal, for example, while the bristles 141 of the central portion 144 may be formed from a softer polymer.

In operation, the surgeon may hold the cleaning brush 137 by the handle portion 139 and position the cleaning brush 137 such that the sternum 110 is partially disposed within the cleaning channel 148, with the cut surface 124 being flush with the central portion 144 of bristles 141. Then, the surgeon may move the cleaning brush 137 along the cut surface 124 to clean and/or prepare the cut surface for the adhesive 34, shown in FIG. 2. As the cleaning brush 137 is moved, the central portion 144 cleans the cut surface 124, while the outer portions 145 clean the anterior surface 118 and a posterior surface 149 of the sternum 110. Since the bristles 141 of the central portion 141 are relatively soft, they present a low risk of damaging the substantially porous structure of the more fragile cancellous bone 128 that is exposed at the cut surface 124, particularly for osteoporotic patients. The more rigid bristles 141 of the outer portions 145 simultaneously clean the cortical bone 126 at the anterior surface 118 and the posterior surface 149 of the sternum 110, where greater forces are acceptable. The relative rigidity of the bristles 141 of the outer portions 145 act to scrape soft tissue and other contaminants away from the bone more aggressively than would be possible with softer bristles 141. In some embodiments, the cleaning brush 137 may also be configured such that the outer portions 145 clean the portions of cortical bone 126 exposed at the cut surfaces 124 in addition to the anterior surface 118 and the posterior surface 149 of the sternum 110.

Figure 7:
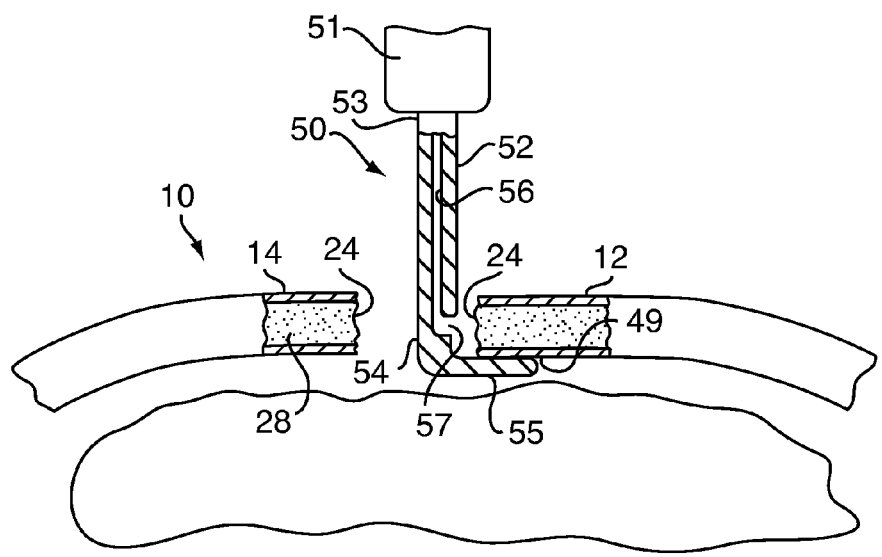
FIG. 7 is a side cross-sectional view an embodiment of a cleaning nozzle according to the present invention.

Referring to FIG. 7, in some embodiments, the use of carbon dioxide or other gases or liquids may be used to prepare the cut surfaces 24. For instance, a cleaning nozzle 50 may be provided for use with a variety of commercially available lavage systems 51, such as the CarboJet® lavage system, available from Kinamed®, Inc. of Camarillo, Calif. The cleaning nozzle 50 preferably protects the organs under the sternum 10 while preparing and/or drying the cut surfaces 24.

Figure 8:
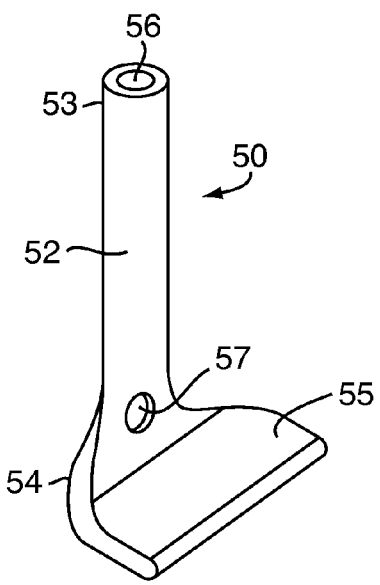
FIG. 8 is a side perspective view of the cleaning nozzle of FIG. 7.

Referring to FIGS. 7 and 8, the cleaning nozzle 50 preferably includes a nozzle body 52 extending longitudinally from a first end 53 adapted to connect to the lavage system 51 to a second end 54 having a protective blade 55 attached thereto. The protective blade 55 may be integrally formed at the second end 54 of the nozzle body 52 or may be provided as a separate attachment that may be fastened to the second end 54. The nozzle body 52 has at least one fluid channel 56 extending therethrough from the first end 53 to an outlet 57 located just above the protective blade 55. The at least one fluid channel 56 is in fluid communication with the lavage system 51 when the cleaning nozzle 50 is connected thereto. The outlet 57 may be circular in shape or, alternatively, may take the shape of a slot (e.g. rectangular or elliptical) to distribute cleaning fluid from the lavage system 51 over a broad surface area with a single pass of the cleaning nozzle 50. In some embodiments, the fluid channel 56 and the outlet 57 may be adapted to distribute the cleaning fluid substantially parallel to the protective blade 55, while in other embodiments, the fluid channel 56 and the outlet 57 may be adapted to distribute the cleaning fluid at a downward angle toward the protective blade 55, for example, at an angle of approximately forty-five degrees (45°).

Referring back to FIG. 7, in operation, the surgeon may attach the cleaning nozzle 50 to the lavage system 51 and then insert the cleaning nozzle 50 between the cut surfaces 24 of the first sternum portion 12 and the second sternum portion 14. The surgeon then moves the cleaning nozzle 50 such that the protective blade 55 extends, at least partially, under one of either the first sternum portion 12 or the second sternum portion 14 with the outlet 57 facing the cut surface 24 of the sternum portion under which the protective blade 55 is extending. Preferably, the surgeon may even bring the protective blade 55 into contact with the posterior surface 49 of the respective first sternum portion 12 or second sternum portion 14. The surgeon may then activate the lavage system 51 to send the cleaning liquid or gas through the at least one fluid channel 56 of the cleaning nozzle 50 and out through the outlet 57. As the cleaning liquid or gas exits the outlet 57, it sprays against the cut surface 24 to remove contaminants from the cut surface 24. The protective blade 55 prevents the pressurized cleaning liquid or gas from contacting sensitive organs, tissue or similar sensitive structures under the sternum 10 when the cleaning liquid or gas is exiting the cleaning nozzle 50. Thus, the cleaning nozzle 50 advantageously allows a high pressure stream of cleaning liquid or gas to be directed at the cut surface 24, while simultaneously protecting sensitive organs from contact with the high pressure stream.

Figure 9:
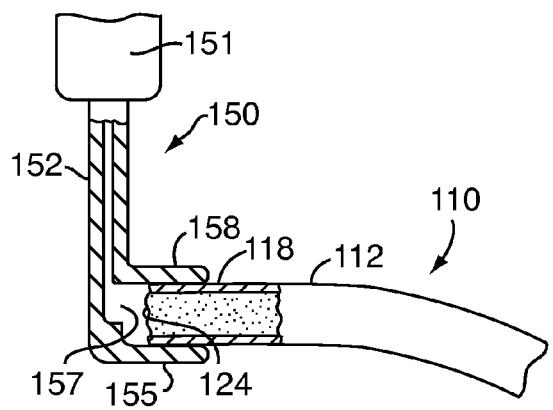
FIG. 9 is a side cross-sectional view of another embodiment of a cleaning nozzle according to the present invention.

Referring to FIG. 9, in some embodiments, the cleaning nozzle 150 may also include a top blade 158 that is substantially parallel to the protective blade 155 and is attached to the nozzle body 152 with the outlet 157 located therebetween. In operation, cleaning nozzle 150 is situated with the cut surface 124 of the first sternum portion 112 or the second sternum portion 114 located between the protective blade 155 and the top blade 158. The top blade 158 constrains the cleaning nozzle 150 by contacting the anterior surface 118 of the sternum 110 to advantageously prevent unintentional movement of the cleaning nozzle 150 into the sensitive structure under the sternum 110. Then, when the lavage system 151 is activated, the pressurized stream of cleaning liquid or gas exits the outlet 157 to clean the cut surface 124 and is advantageously contained between the protective blade 155 and the top blade 158. Thus, as discussed above, the cleaning nozzle 150 protects the sensitive organs from contact with the high pressure stream of cleaning liquid or gas. Additionally, the top blade 158 may also act as a shield to limit spray of the cleaning liquid or gas from escaping the incision 16, shown in FIG. 1, and contacting the surgeon and/or any other staff present in the operating room. In some embodiments, a separate shield may be provided that is attachable to the cleaning nozzle 150 to prevent spray of the cleaning liquid or gas from escaping the incision 16, shown in FIG. 1, and contacting the surgeon and/or any other staff present in the operating room.

Figure 10:
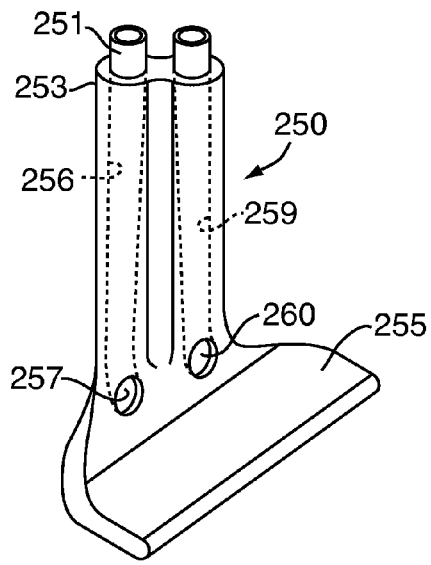
FIG. 10 is a side perspective view of yet another embodiment of a cleaning nozzle according to the present invention.

Referring to FIG. 10, in some embodiments, the lavage system 251 may use cleaning nozzle 250 designed to prepare the cut surface 24, shown in FIG. 7, and to apply the adhesive 34, shown in FIG. 2, at substantially the same time. The cleaning nozzle 250 includes the at least one fluid channel 256 extending therethrough from the first end 253 to the outlet 257 located just above the protective blade 255. The cleaning nozzle 250 also includes a second fluid channel 259 extending therethrough from the first end 253 to a port 260, which may be formed in the cleaning nozzle 250 above the protective blade 255 next to the outlet 257. The at least one fluid channel 256 is in fluid communication with the lavage system 251 when the cleaning nozzle 250 is connected thereto, while the second fluid channel 259 may be operatively connected to a adhesive delivery system (not shown).

In operation, the surgeon may position the cleaning nozzle 250 in a manner similar to that discussed above by positioning the cleaning nozzle 250 with the protective blade 255 extending, at least partially, under one of either the first sternum portion 12, shown in FIG. 7, or the second sternum portion 14, shown in FIG. 7, with the outlet 257 facing the cut surface 24, shown in FIG. 7. The surgeon may then activate the lavage system 251 to send the cleaning liquid or gas through the at least one fluid channel 256 of the cleaning nozzle 250 and out through the outlet 257 to prepare the cut surface 24, shown in FIG. 7, by removing contaminants. The surgeon may then activate the adhesive delivery system (not shown) to deliver adhesive 34, shown in FIG. 2, to the cut surface 24, shown in FIG. 7, through the second fluid channel 259 and the port 260. Thus, the surgeon is able to clean the cut surface 24, shown in FIG. 7, using the lavage system 251 and then apply the adhesive 34, shown in FIG. 2, to the cut surface 24, shown in FIG. 7, before surface contamination can occur. In some embodiments, the surgeon may activate the lavage system 251 and the adhesive delivery system (not shown) at substantially the same time so that the adhesive 34, shown in FIG. 2, is delivered to the cut surface 24, shown in FIG. 7, through the port 260 substantially immediately after the cut surface 24, shown in FIG. 7, is prepared by cleaning fluid passing through the outlet 257. This embodiment may be particularly beneficial where the cleaning fluid is carbon dioxide gas, since the gas lavage actively dries the cut surface 24, shown in FIG. 7, preparing the cut surface 24, shown in FIG. 7, for immediate application of the adhesive 34, shown in FIG. 2. In these embodiments, the protective blade 255 advantageously prevents both the pressurized cleaning liquid or gas and the adhesive 34, shown in FIG. 2, from contacting sensitive organs, tissue or similar sensitive structures under the sternum 10, shown in FIG. 7.

Still referring to FIG. 10, in some embodiments, the second fluid channel 259 and port 260 may be operatively connected to a vacuum system (not shown) rather than the adhesive delivery system (not shown) discussed above. In these embodiments, the vacuum system may be activated at the same time as the lavage system 251 to remove the cleaning liquid or gas, as well as any contaminants removed from the cut surface 24, shown in FIG. 7, from the operative site. Embodiments having the vacuum system (not shown) may be particularly advantageous for lavage systems 251 using cleaning liquids, such as water or the like.

Figure 11:
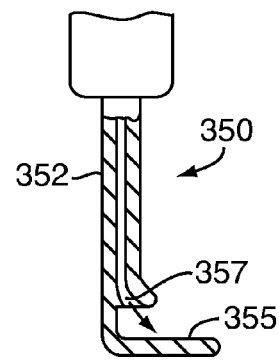
FIG. 11 is a side cross-sectional view of a further embodiment of a cleaning nozzle according to the present invention.

Although the various cleaning nozzles 50, 150 and 250 have been described as including outlets 57, 157 and 257 to direct cleaning liquid or gas approximately perpendicular to the cut surface 24, shown in FIG. 7, referring to FIG. 11, the outlet 357 may also be formed at an angle to direct the cleaning liquid or gas at a different direction relative to the cut surface 24, shown in FIG. 7. In these embodiments, the protective blade 355 still serves to prevent the pressurized cleaning liquid or gas from contacting sensitive organs, tissue or similar sensitive structures under the sternum 10, shown in FIG. 7.

Figure 12:
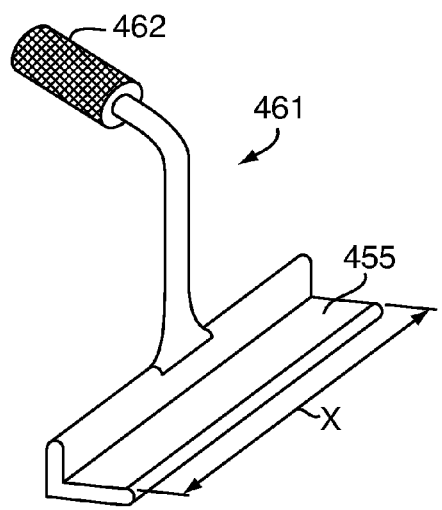
FIG. 12 is a side perspective view of an embodiment of a protection tool according to the present invention.

Referring to FIG. 12, in some embodiments, a protection tool 461 may be formed as a standalone instrument including the protective blade 455 having a handle 462 attached thereto. In operation, the surgeon may position the protective blade 455 proximate to the cut surface 24, shown in FIG. 7, using the handle 262. The surgeon may then prepare the cut surface 24, shown in FIG. 7, using the lavage system 251 and an off-the-shelf nozzle (not shown) without modification, while preventing the pressurized cleaning liquid or gas from contacting sensitive organs, tissue or similar sensitive structures under the sternum 10, shown in FIG. 7, using the standalone protection tool 461. This embodiment is advantageous since it allows the surgeon to use the off-the-shelf nozzle (not shown) and lavage system 251 without modifications. Additionally, since the protective blade 455 of the standalone protection tool 461 is decoupled from the off-the-shelf nozzle (not shown), the protective blade 455 may be formed to a length X sufficient to protect the entire cut surface 24, shown in FIG. 7, without moving.

Figure 13:
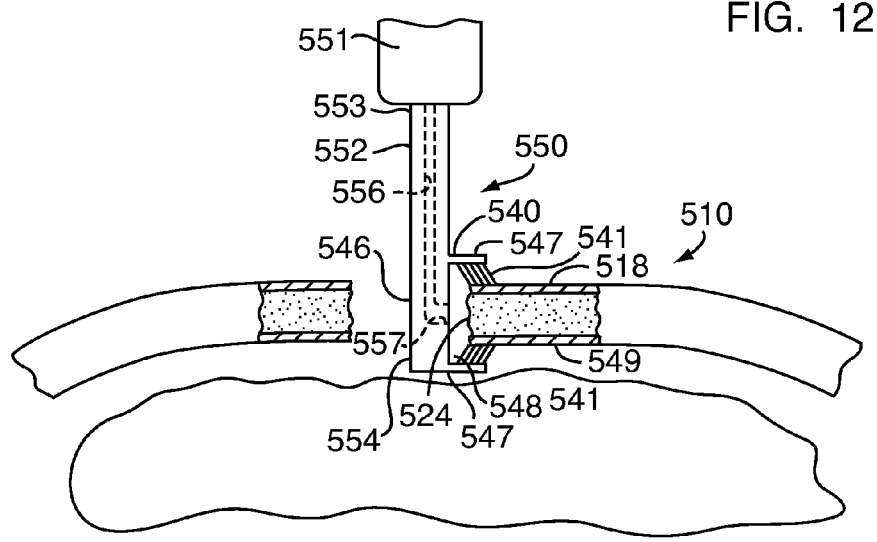
FIG. 13 is a side cross-sectional view an embodiment of an integrated cleaning nozzle and brush head according to the present invention.

Referring to FIG. 13, in another embodiment of the present invention, the cleaning nozzle 550 may be integrated with a brush head 540, similar to the brush head 40, shown in FIG. 6, of the cleaning brush 137, shown in FIG. 6. The cleaning nozzle 550 includes a nozzle body 552 extending from a first end 553 adapted to connect to the lavage system 551 to a second end 554 having the brush head 540 formed thereon. The brush head 540 may include a central base portion 546 flanked on each side thereof by substantially perpendicular outer base portions 547 to form a cleaning channel 548. The outer base portions 547 may have bristles 541 disposed thereon. The nozzle body 552 has at least one fluid channel 556 extending therethrough from the first end 553 to an outlet 557 located on the central base portion 546. The at least one fluid channel 556 is in fluid communication with the lavage system 551 when the cleaning nozzle 550 is connected thereto.

Similar to the embodiments discussed above, the outlet 557 may be circular in shape or, alternatively, may take the shape of a slot (e.g. rectangular or elliptical) to distribute cleaning fluid from the lavage system 551 over a broad surface area with a single pass of the cleaning nozzle 550. In some embodiments, the fluid channel 556 and the outlet 557 may be adapted to distribute the cleaning fluid substantially parallel to the outer base portions 547, while in other embodiments, the fluid channel 556 and the outlet 557 may be adapted to distribute the cleaning fluid at a downward angle toward the lower outer base portion 547, for example, at an angle of approximately forty-five degrees (45°).

In operation, the surgeon may hold the position the cleaning nozzle 550 such that the sternum 510 is partially disposed within the cleaning channel 548. The surgeon may then activate the lavage system 551 to send the cleaning liquid or gas through the at least one fluid channel 556 of the cleaning nozzle 550 and out through the outlet 557. The surgeon may move the cleaning nozzle 550 along the cut surface 524 to clean and/or prepare the cut surface for the adhesive 34, shown in FIG. 2. As the cleaning nozzle 550 moves, cleaning fluid exiting the outlet 557 and sprays against the cut surface 524 thereby cleaning the cut surface 524. Additionally, the bristles 541 on the outer base portions 547 clean the anterior surface 518 and the posterior surface 549 of the sternum 510. The outer base portions 547 also act as the protective blades 55, shown in FIG. 7, preventing the pressurized cleaning liquid or gas from contacting sensitive organs, tissue or similar sensitive structures under the sternum 510 when the cleaning liquid or gas is exiting the cleaning nozzle 550.

Although the cleaning nozzles 50, 150, 250, 350 and 550 and the protection tool 461 have been described for use in preparing cut surfaces 24, shown in FIG. 7, of the sternum 10, shown in FIG. 7, it should be understood by those skilled in the art that the cleaning nozzles 50, 150, 250, 350 and 550 and the protection tool 461 may also be used to prepare other bone surfaces, particularly those in the proximity of sensitive structures. For example, the cleaning nozzles 50, 150, 250, 350 and 550 and the protection tool 461 may be designed to clean cranial bone, with the protective blade 55, 155, 255, 355 and 455 or outer base portions 547 protecting the brain during the cleaning.

Figure 14:
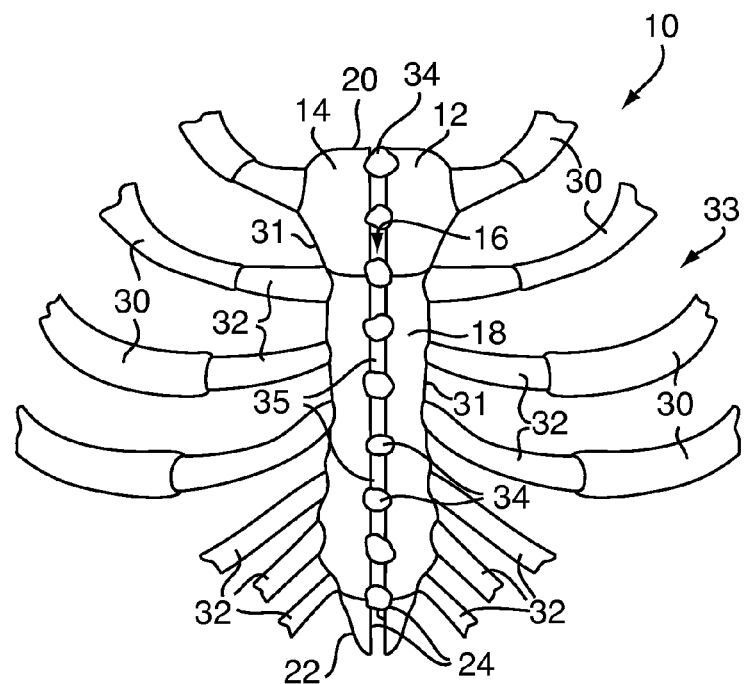
FIG. 14 is a front view of the separated sternum of FIG. 1 with adhesive placed therein in accordance with another embodiment of the present invention.

Referring to FIG. 14, when the adhesive 34 is applied to the cut surface 24, both the size and frequency of application of adhesive 34 along the longitudinal incision 16 may be varied to alter the bond strength between the first and second sternum portions 12 and 14. Additionally, the size and/or frequency of application of adhesive 34 may be changed to increase the size and frequency of gaps 35, thereby providing more bone to bone contact between the first and second sternum portions 12 and 14 to promote additional natural bone growth, when the first and second sternum portions 12 and 14 are compressed together as discussed above in connection with FIG. 3.

Figure 15:
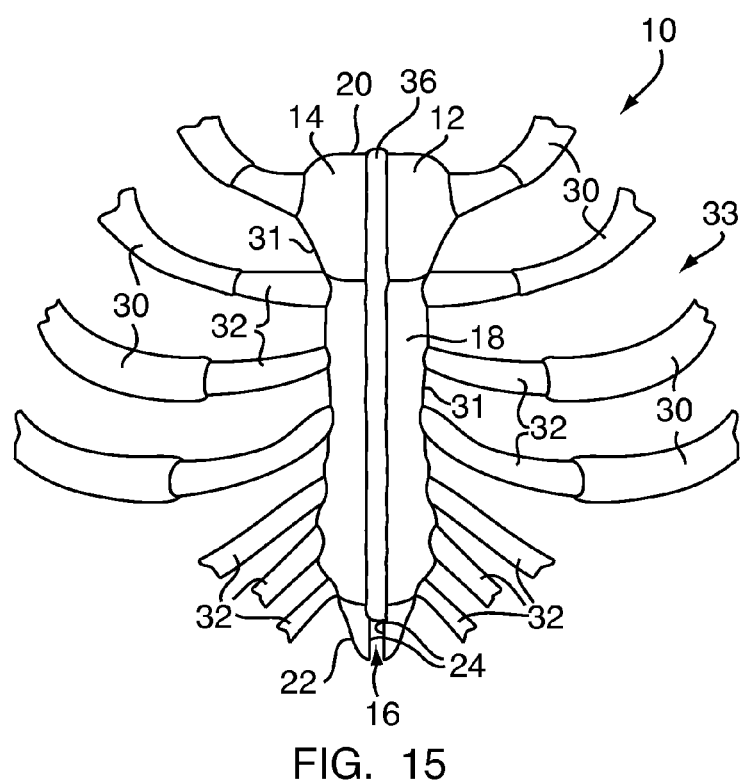
FIG. 15 is a front view of the separated sternum of FIG. 1 with adhesive placed therein in accordance with another embodiment of the present invention.

Referring to FIG. 15, in some embodiments of the present invention, the adhesive 34 may be applied over substantially the entire length of the incision 16 to increase the strength of the bond between the first and second sternum portions 12 and 14. In this embodiment, it may be particularly advantageous for the adhesive 34 to have osteoconductive properties so that bone growth between the first and second sternum portions 12 and 14 occurs through the adhesive 34, thereby allowing the patient to heal.

Figures 16, 17A, 18A, 19A:
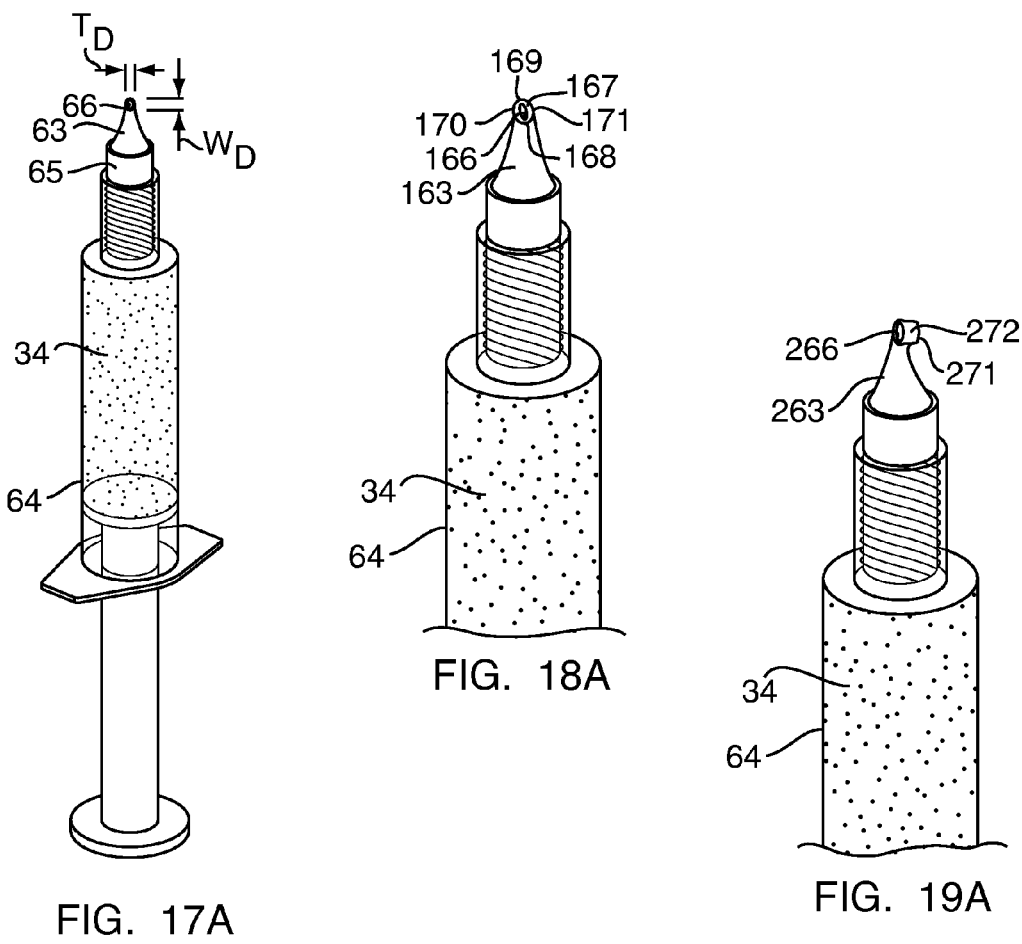
FIG. 16 is a side perspective view of a sternum portion of FIG. 1 with adhesive applied thereon according to yet another embodiment of the present invention.
FIG. 17A is a side perspective view of an embodiment of an adhesive application device according to the present invention.
FIG. 18A is a side perspective view of an embodiment of an adhesive applicator tip according to the present invention.
FIG. 19A is a side view of another embodiment of an adhesive applicator tip according to the present invention.

Referring to FIG. 16, in some embodiments of the present invention, the adhesive 34 may be applied to substantially only the cancellous bone 28 and not to the cortical bone 26. The adhesive 34 may be applied to the cancellous bone 28 over substantially the entire length of the incision 16, shown in FIG. 1, or intermittently to vary the strength of the adhesive bond formed, as discussed above. The application of the adhesive 34 to solely the cancellous bone 28 provides for a direct interface between the cortical bone 26 of the first and second sternum portions 12 and 14, shown in FIG. 1, which may allow new bone formation and growth to quickly bridge the incision 16 at the interface between the cortical bone 26 of the first sternum portion 12 and the cortical bone 26 of the second sternum portion 14, shown in FIG. 1. Since the cortical bone 26 accounts for a majority of the strength of the sternum 10, shown in FIG. 1, providing faster bone formation and growth across the interface between the cortical bone 26 of the first sternum portion 12 and the cortical bone 26 of the second sternum portion 14, shown in FIG. 1, may more quickly restore the sternum 10, shown in FIG. 1, to its pre-operative strength.

Referring to FIGS. 17A-17C, an applicator tip 63 for applying adhesive 34 to the cut surfaces 24, shown in FIG. 1, using a syringe 64 is shown. Referring to FIG. 17A, the applicator tip 63 includes a base 65 that is connectable to an adhesive reservoir such as the syringe 64 and a dispenser outlet 66 that is preferably formed to be non-circular. The dispenser outlet 66 preferably has a width $W_D$ that is approximately equal to the sternum thickness $T_{sternum}$, shown in FIG. 6, and a thickness $T_D$ that is selected to control the rate at which adhesive 34 exits the applicator tip 63 through the outlet 66. Referring to FIG. 17B, preferably, the width $W_D$ is greater than the thickness $T_D$, for example, to provide the outlet 66 with an elliptical shape, as shown, an oval shape, a rectangular shape or the like. Referring to FIG. 17A, the base 65 may be connectable to the syringe 64 through known fastening means such as male/female thread configurations, as shown, female/male thread configurations, a Luer Lock connection or the like. In operation, the applicator tip 63 allows the surgeon to dispense a broad bead or ribbon of adhesive 34 that is approximately the thickness of the sternum 10, shown in FIG. 1, and is not overly thick. Accordingly, the applicator tip 63 may advantageously allow the surgeon to apply adhesive 34 to the cut surface 24, shown in FIG. 1, with a single pass along the incision 16, shown in FIG. 1. This is unlike a traditional needle/syringe combination, which dispenses material through a small circular bore and, therefore, requires multiple passes along the incision 16, shown in FIG. 1, to achieve full coverage of the cut surfaces 24, shown in FIG. 1.

Referring to FIGS. 18A-18C, in some embodiments, the dispenser outlet 166 of the applicator tip 163 may include a bevel 167 angling the dispenser outlet 166 along the thickness $T_D$ from a leading edge 170 to a trailing edge 171. The bevel 167 may also angle the dispenser outlet 166 along the width $W_D$ from an inner edge 168 to an outer edge 169 and, in some embodiments, the bevel may angle the dispenser outlet 166 along both the width $W_D$ and the thickness $T_D$. By angling the dispenser outlet 166 along the width $W_D$, the bevel 167 may facilitate dispensing of the adhesive 34, shown in FIG. 18A, from outside of the incision 16, shown in FIG. 1, while holding the syringe 64, shown in FIG. 18A, at an oblique angle relative to the cut surface 24, shown in FIG. 1. By angling the dispenser outlet 166 along the thickness $T_D$, the applicator tip 163 may be positioned and moved relative to the cut surface 24, shown in FIG. 1, such that the trailing edge 171 of the bevel 167 drives the adhesive 34, shown in FIG. 18A, exiting the dispenser outlet 166 into the pores of the cancellous bone 26, shown in FIG. 1, through the cut surface 24, shown in FIG. 1, as the trailing edge 171 passes over adhesive 34, shown in FIG. 18A. The trailing edge 171 may also maintain a thin uniform layer of adhesive 34, shown in FIG. 18A, along the cut surface 24, shown in FIG. 1. In some embodiments, the applicator tip 163 may be formed with a measure of flexibility to increase resistance between the trailing edge 171 and the cut surface 24, shown in FIG. 1, to better drive the adhesive 34, shown in FIG. 18A, into the cut surface 24, shown in FIG. 1, as the trailing edge 171 passes over the exiting adhesive 34, shown in FIG. 18A.

Referring to FIGS. 19A-19C, in other embodiments, the applicator tip 263 may also include a flexible extension 272 at the trailing edge 271 thereof to further increase resistance with the cut surface 24, shown in FIG. 1. In operation, the flexible extension 272 passes over the adhesive 34, shown in FIG. 19A, immediately after the adhesive 34, shown in FIG. 19A, exits the dispenser outlet 266. As the flexible extension 272 passes over the adhesive 34, shown in FIG. 19A, the flexible extension 272 pushes the adhesive 34, shown in FIG. 19A, into the pores of the cancellous bone 28, shown in FIG. 1, and maintains a thin uniform layer of adhesive 34, shown in FIG. 19A, along the cut surface 24, shown in FIG. 1. By pushing the adhesive 34, shown in FIG. 19A, into the cancellous bone 28, shown in FIG. 1, the trailing edge 271 or flexible extension 272 advantageously improves mechanical interlocking between the adhesive 34, shown in FIG. 19A, and the first and second sternum portions 12 and 14, shown in FIG. 1, once the adhesive 34, shown in FIG. 19A, cures.

Referring to FIG. 20A, in another embodiment, the applicator tip 363 may include a resilient sidewall 373 extending from the base 365 to the dispenser outlet 366. The resilient sidewall 373 includes a plurality of pleats or waves 374 formed therein extending from the base 365 to the dispenser outlet 366. The plurality of pleats or waves 374 provides the dispenser outlet 366 with a circumference 375 having ridges 376 and troughs 377 that define a first dispenser cross-sectional area A.

In operation, the adhesive 334 is dispensed from the syringe 364 through the applicator tip 363 and onto the cut surface 24, shown in FIG. 1. While the adhesive 334 is in a liquid state, a light pressure is sufficient to expel the adhesive 334 from the syringe 364 and through the first dispenser cross-sectional area A of dispenser outlet 366. However, as the adhesive 334 begins to polymerize and become more viscous, a greater pressure is required to pass the adhesive 334 though the first dispenser cross-sectional area A of the dispenser outlet 366. This increase in pressure causes the troughs 377 of the resilient sidewall 373 to push outward, changing the shape of the resilient sidewall 373, thereby providing the dispenser outlet 366 with a larger, second cross-sectional area B, shown in FIG. 20B. Referring to FIG. 20B, the larger second cross-sectional area B allows the more viscous adhesive 334 to pass through the dispenser outlet 366, without the need for a high pressure delivery system, such as a hydraulic system, a thread assisted system or the like. Then, when the surgeon finishes dispensing the adhesive 334 the applicator tip 363 may return to its original shape, having the first dispenser cross-sectional area A, shown in FIG. 20A, or the applicator tip 363 may remain in the altered shape, having cross-sectional area B, shown in FIG. 20B, due to adhesive 334 remaining within the applicator tip 363 and preventing a return to the original shape. Although the second cross-sectional area B is shown as being substantially circular, one skilled in the art will appreciate that the second cross-sectional area B may be formed in both circular and non-circular shapes, such as those discussed above.

Figure 21:
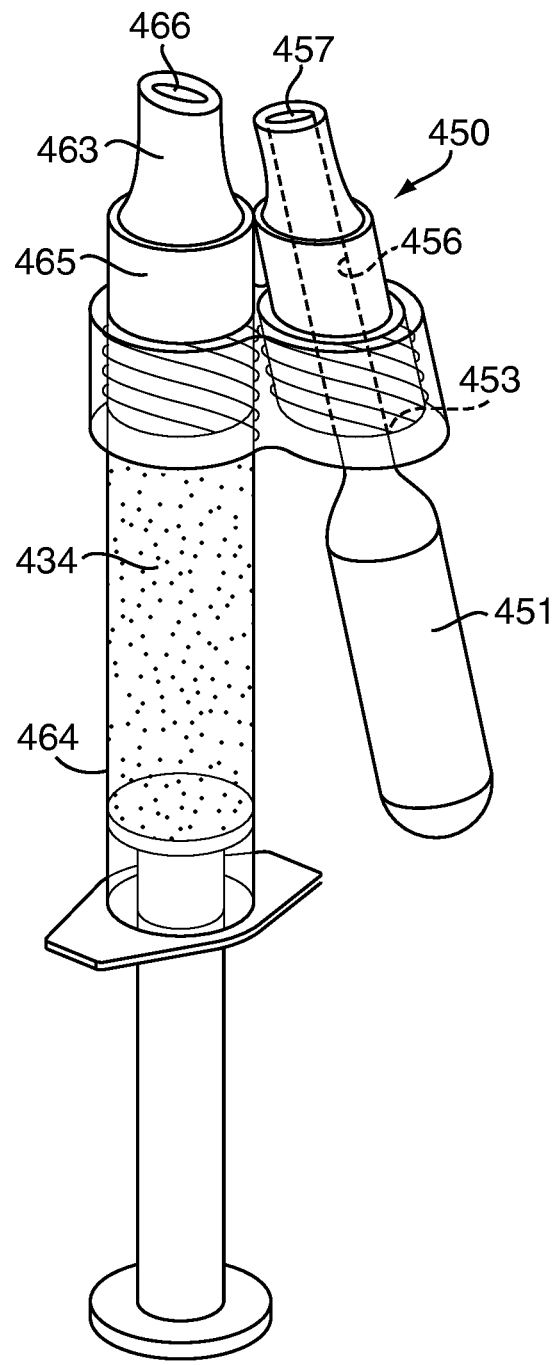
FIG. 21 is a side perspective view of an applicator tip according to yet another embodiment of the present invention.

Referring to FIG. 21, in some embodiments, the applicator tip 463 may be integrated with the cleaning nozzle 450 into a single unit designed to both prepare the cut surface 24, shown in FIG. 1, and to apply adhesive 434 thereto. The applicator tip 463 includes base 465 that is connectable to syringe 464 for supplying adhesive 434 and dispenser outlet 466 for dispensing the adhesive 434 onto the cute surface 24, shown in FIG. 1. The cleaning nozzle 450 includes fluid channel 456 extending therethrough from first end 453 to outlet 457. The first end is connectable to lavage system 451 for supplying cleaning fluid to the fluid channel 456. The lavage system may be, for example, a commercial lavage system such as that discussed in connection with FIG. 7, a carbon dioxide canister or similar canister of compressed gas, a system for supplying pressurized air, or the like. In some embodiments, the first end may be connectable to a vacuum system (not shown) to remove contaminants from the cut surface 24, shown in FIG. 1, by applying suction through the fluid channel 456. The outlet 457 is preferably disposed proximate to the dispenser outlet 465 such that the cleaning fluid expelled from the outlet 457 is applied to the cut surface 24, shown in FIG. 1, at substantially the same location as the adhesive 434 applied through the dispenser outlet 465. In some embodiments, the fluid channel 456 may be angled relative to the applicator tip 463 to expel the cleaning fluid from the outlet 457 to substantially the same location on the cut surface 24, shown in FIG. 1, as the adhesive 434 applied through the dispenser outlet 465. By providing the applicator tip 463 and the cleaning nozzle 450 in a single unit, adhesive 434 may be applied to the cut surface 24, shown in FIG. 1, substantially immediately after the cut surface 24, shown in FIG. 1, is cleaned with cleaning fluid, which reduces contamination of the adhesive 434 from bodily fluids or the like.

Figure 22:
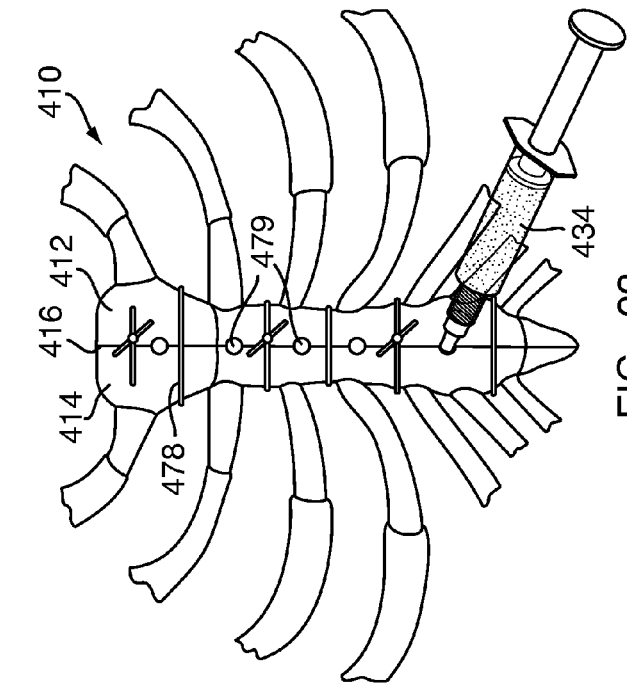
FIG. 22 is a front view of the separated sternum with adhesive placed therein of FIG. 2 with an additional compression device.

Referring to FIG. 22, the method for sternum closure of the present invention may also include securing the first and second sternum portions 12 and 14 together with compressive devices 78 that are permanent, such as wires, cables, bands or straps that pass around the sternum to hold the first and second sternum portions 12 and 14 together. The compressive devices 78 may be positioned around the sternum 10 while the adhesive 34 is in the liquid or taffy-like state to maintain the position of the first and second sternum portions 12 and 14 proximate to one another while the adhesive 34 cures to form the adhesive bond discussed above. In this embodiment, the compressive devices 78 provide the compressive force for securing the first sternum portion 12 and the second sternum portion 14 together during the healing process, thereby ensuring that the sternum portions 12 and 14 do not separate. The adhesive bond formed by adhesive 34 inhibits flexing and shearing motion of the first and second sternum portions 12 and 14 relative to one another, which would still be possible if the first and second sternum portions 12 and 14 were secured by only compressive devices 78. Inhibiting relative movement between the first and second sternum portions 12 and 14 with the adhesive 34 may also reduce the degree to which the compressive devices 78 cut into the sternum 10, preventing loosening of the compressive devices 78, separation of the closed sternum 10 and potential discomfort to the patient.

Additionally, by using the adhesive 34 with the compressive devices 78, relatively fewer compressive devices 78 may be used to secure the sternum portions, when compared to conventional sternal closure devices. For example, in addition to the adhesive 34, the present invention may use only two compressive devices 78, one at either end of the sternum 10, to provide adequate stability to the closed sternum 10. Reducing the number of compressive devices 78, such as wires, may decrease the risk of injury to the patient, because fewer wires or cables must be passed behind the sternum 10 and across surgical grafts both during the initial procedure and during revision surgery, if necessary.

In some embodiments, the compressive devices 78 may be formed from a resorbable material such as a resorbable polymer or the like. For example, the compressive devices 78 may be formed as resorbable polymer cable ties or similar fastening devices. Resorbable compressive devices 78 may advantageously reduce an implant profile of the compressive devices 78 over time as the compressive devices 78 resorb. Additionally, using adhesive 34 with the resorbable compressive devices 78 may overcome the deficiencies typically associated with resorbable polymers such as their inability to maintain a stable closure (i.e. stretching over time and slipping of closure knots) because the adhesive 34 may aid in maintaining the bond between the first and second sternum portions 12 and 14 and may prevent relative movement therebetween.

Figure 23:
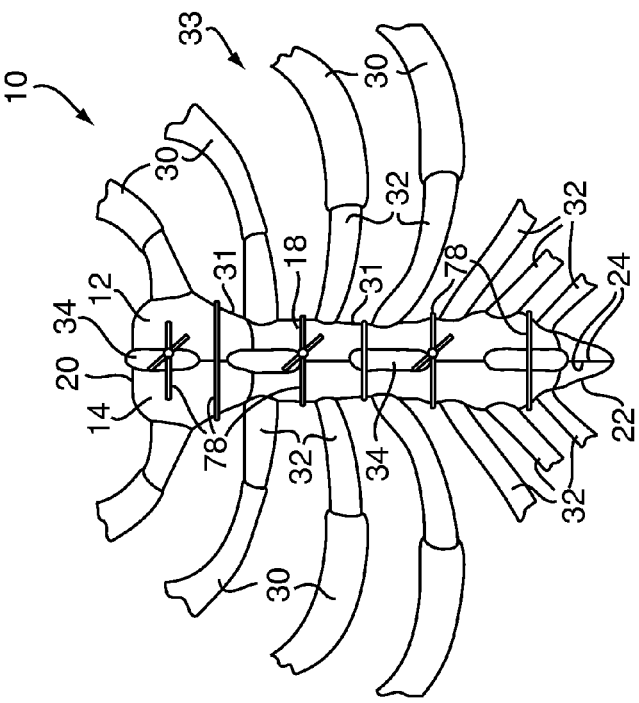
FIG. 23 is a front view of a separated sternum secured by compression devices according to another embodiment of the present invention.

Referring to FIG. 23, in some embodiments, the adhesive 434 may be applied to the incision 416 after the compressive devices 478 are secured to the sternum 410. For instance, after the compressive devices 478 have been secured to the sternum 410, injection holes 479 may be drilled at various points along the incision 416. The adhesive 434 may then be injected through the injection holes 479 into the cancellous bone 28, shown in FIG. 1, where it may expand into the porous structure of the cancellous bone 28, shown in FIG. 1, and cure to form a rigid mechanical connection between the first and second sternum portions 412 and 414. In some embodiments, a vacuum (not shown) may be applied to one or more of the injection holes 479 while adhesive is being injected through another injection hole 479 to provide suction and improve migration of the adhesive 434 within the incision 416 as it is injected therein.

Figure 24:
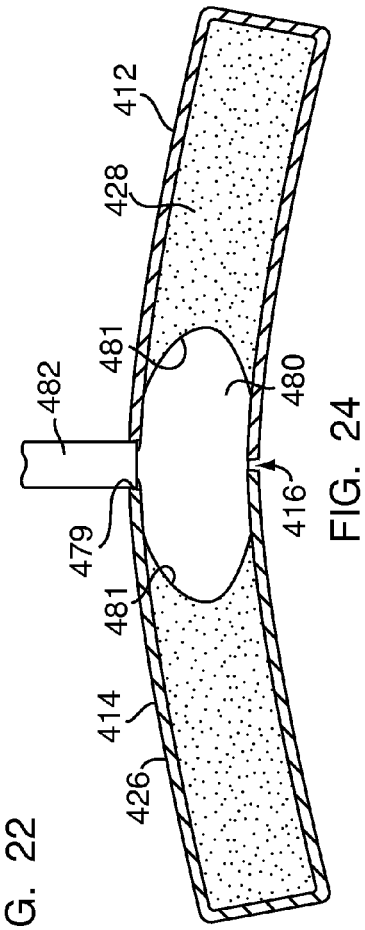
FIG. 24 is a cross-sectional view of an embodiment for applying adhesive to the sternum secured by compression devices of FIG. 23.

Referring to FIG. 24, prior to injection of the adhesive 434, shown in FIG. 23, through the injection holes 479, in some embodiments, a balloon 480 may be used to form voids 481 in the cancellous bone 428 to accommodate the adhesive 434, shown in FIG. 23. In operation, the balloon 480 may be inserted through a cannula 482 and into the injection hole 479. Once in the injection hole 479, the balloon 480 may be inflated causing it to expand and compress the cancellous bone 428. Since the injection hole 479 is formed at the incision 416, the balloon 480 will compress the cancellous bone 428 of both the first and second sternum portions 412 and 414 simultaneously. The balloon 480 may then be deflated and withdrawn from the injection hole 479, leaving a void behind. The adhesive 434, shown in FIG. 23, may then be injected into the injection hole 479 as discussed above and allowed to polymerize to form the rigid mechanical connection between the first and second sternum portions 412 and 414. As should be appreciated by those skilled in the art, the balloon is preferably formed to facilitate expansion into the cancellous bone 428 and not the cortical bone 426 when inflated, for example, the balloon 480 may be formed to inflate in a disc shape.

Figure 25:
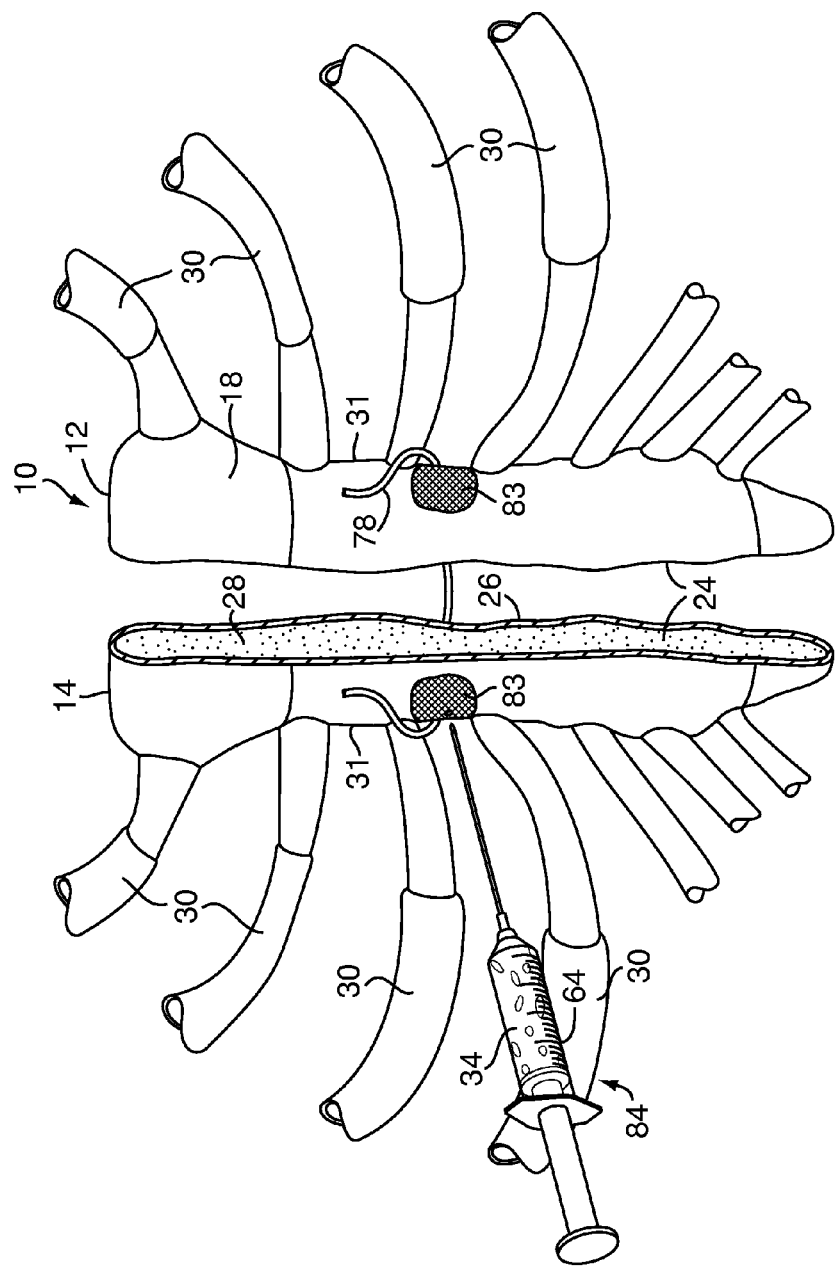
FIG. 25 is a perspective view of another embodiment of the separated sternum with adhesive placed therein of FIG. 22.

Referring to FIG. 25, adhesive 34 may also be injected into or through the outer cortical bone 26 of the sternum 10 in contact regions 83 where the compressive devices 78 are in contact with, or will be in contact with, the first and second sternum portions 12 and 14 after the sternum 10 has been closed. For example, the adhesive 34 may be injected with delivery means 84, such as syringe 64 using a cannula, into the sternum 10 through the cortical bone 26 at the anterior surface 18 along the peripheral edges 31 of the sternum 10 between rib bones 30. Alternatively, the adhesive 34 may be delivered to the contact region 83 by injection through the cancellous bone 28 at the cut surface 24. The adhesive 34 occupies space within the porous structure of the cancellous bone 28 and/or cortical bone 26, where it cures to add strength and stiffness to the cancellous bone 28 and/or cortical bone 26 in the contact regions 83. The injected adhesive 34 makes it more difficult for the compressive devices 78 to cut into the bone, thereby preventing loosening of the compressive devices 78 and/or pain experienced by the patient. The application of adhesive 34 to the contact regions 83 may be particularly beneficial for patients with weak osteoporotic bones.

Figure 26:
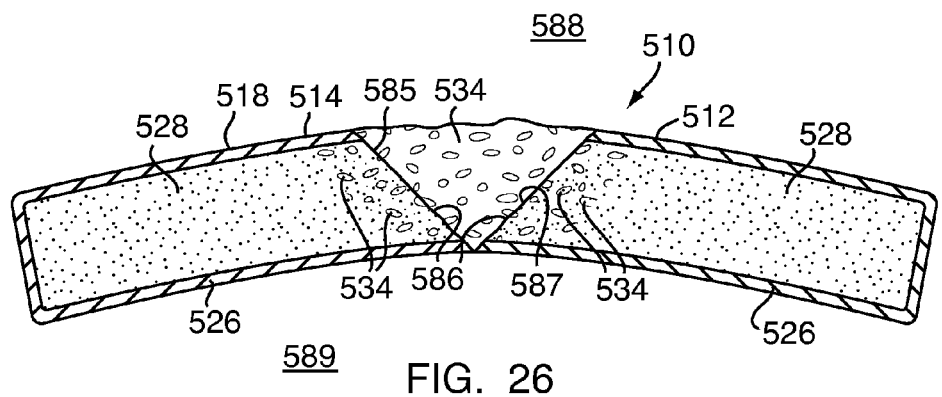
FIG. 26 is a cross-sectional view of another embodiment of the separated sternum with adhesive placed therein of FIG. 2.

Referring to FIG. 26, the method for sternal closure according to another embodiment of the present invention may also include forming interface features 585 in the first and second sternal portions 512 and 514 to facilitate healing and/or increase strength of the bond between the first and second sternum portions 512 and 514. For instance, the cut surfaces 24, shown in FIG. 4, may be formed into chamfers 586, each sloping inward toward the opposing first or second sternum portion 512 or 514. The chamfers 586 may extend over substantially the entire longitudinal length of the sternum 510 or may be located only at intermittent locations, i.e. only where adhesive 534 is to be applied, for example, as shown in the embodiment of FIG. 2.

When the first and second sternum portions 512 and 514 are brought proximate to one another during the sternum closure procedure, the chamfers 586 form a cavity 587, open to and accessible from an anterior 588 of the sternum 510. The cavity 587 may be filled with the adhesive 534 during the adhesive application process. Since the cavity 587 is highly accessible, it makes the process of applying the adhesive 534 easier for practitioners. The chamfers 586 also have an increased surface area with which to bond to the adhesive 534 when compared to the cut surfaces 24, shown in FIG. 4, thereby providing increased strength in the bond formed between the first and second sternum portions 512 and 514. Additionally, any expansion of the adhesive 534 during the curing process is likely to occur outward from the cavity 587 of the sternum 510, rather than into an interior 589 of the thoracic cage (not shown) of the patient, where it could potentially cause damage.

Although shown as chamfers 586, one skilled in the art should understand that the interface features 585 may take other forms that provide an improved interface to facilitate healing and/or increase strength, for example, flanges may be formed in the first and second sternal portions 512 and 514.

Figure 27:
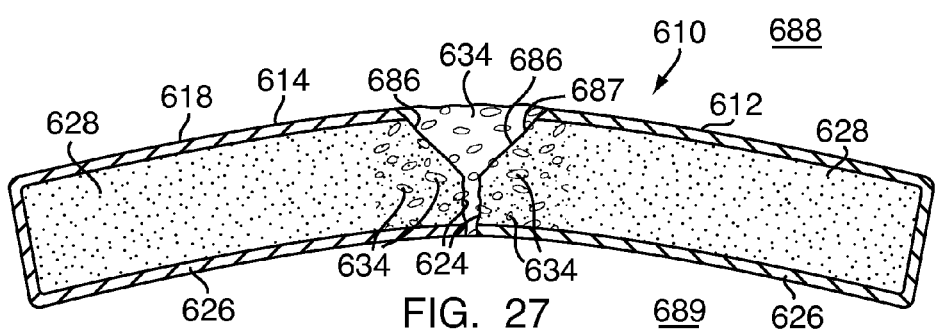
FIG. 27 is a cross-sectional view of another embodiment of the separated sternum with adhesive placed therein of FIG. 2.

Referring to FIG. 27, in another embodiment of the present invention, the cut surfaces 624 of the first and second sternum portions 612 and 614 may be formed with only partial chamfers 686 at the anterior surface 618, with the inner cut surfaces 624 remaining. The chamfers 686 may extend over substantially the entire longitudinal length of the sternum 610 or may be located only at intermittent locations, i.e. only where adhesive 634 is to be applied, for example, as shown in the embodiment of FIG. 2.

When the first and second sternum portions 612 and 614 are brought proximate to one another, during the sternum closure procedure, the cut surfaces 624 contact one another and the chamfers 686 form the cavity 687, open to and accessible from the anterior 688 of the sternum 610. Since the chamfers 686 extend over only a portion of the cut surfaces 624, the cavity 687 is smaller than the cavity 587, shown in FIG. 26. The cavity 687 may be filled with the adhesive 634 as discussed above to form the bond between the first and second sternum portions 612 and 614. The cut surfaces 624 contact one another, thereby allowing for direct bone growth between the first sternum portion 612 and the second sternum portion 614 to promote natural healing after the surgical procedure. Additionally, as discussed in connection with FIG. 26, any expansion of the adhesive 634 during the curing process is likely to occur outward from the cavity 687 of the sternum 610, rather than into the interior 689 of the thoracic cage (not shown) of the patient, where it could potentially cause damage.

Figure 28:
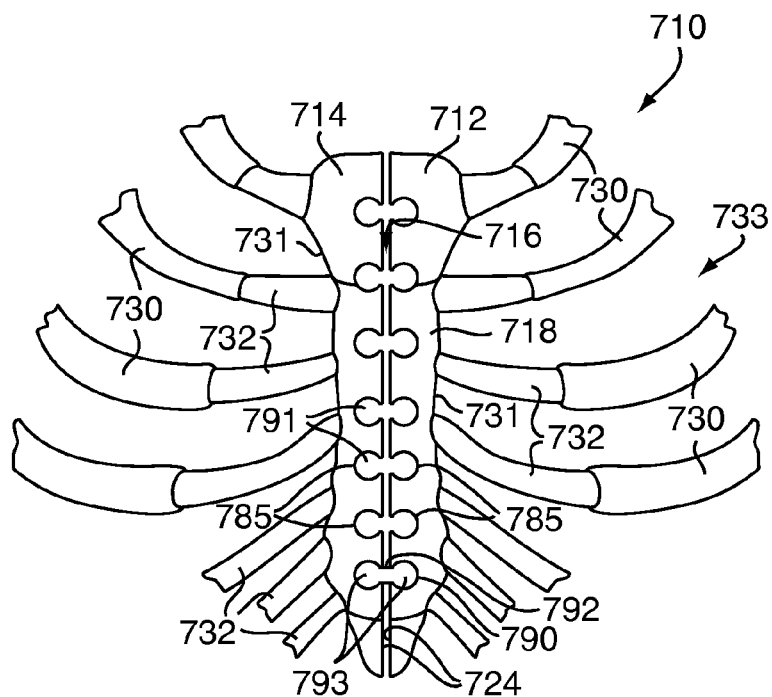
FIG. 28 is a front view of the separated sternum of FIG. 1 with a mechanical joint formed therein in accordance with another embodiment of the present invention.

Referring to FIG. 28, the method for sternal closure according to the present invention may also include inserting a structural member 790 into the interface feature 785 to span the incision 716 between the first and second sternum portions 712 and 714. For instance, interface features 785 may be formed as geometric features 791 for accommodating structural members such as polymeric inserts 792 to provide mechanical joints between the first and second sternum portions 712 and 714. Although shown as polymeric inserts 792, the structural members may also be allograft bone inserts, metal inserts or inserts formed from any other rigid implantable material. The geometric features 791 may be formed to be circular, as shown, or may be formed in various other shapes capable of retaining at least a portion of the polymeric insert 792. The geometric features 791 are formed through the anterior surface 718 of the first and second sternum portions 712 and 714, penetrating the cut surfaces 724 of the first and second sternum portions 712 and 714. The geometric features 791 may extend entirely or, more preferably, only partially through the thickness of the sternum 710. Additionally, the geometric features 791 are preferably formed to be substantially opposite one another on opposing first and second sternum portions 712 and 714 to ease insertion of the polymeric insert 792.

The polymeric insert 792 is formed with end locks 793 which correspond to the shape of geometric features 791, for example, if the geometric features 791 are round, the polymeric insert 792 may be provided with round end locks 793. Similarly, if the geometric features 791 are formed in a triangular shape, the polymeric insert 792 may be formed in a bowtie shape with end locks 793 to be accommodated within the geometric features 791. Preferably, the polymeric inserts 792 are formed from a material that has osteoconductive properties to promote bone growth as the sternum 710 heals after closure. Even more preferably, the polymeric inserts 792 are formed from substantially the same material as the adhesive 34, shown in FIG. 2.

During the sternal closure procedure, the practitioner forms the geometric features 791 in the first and second sternum portions 712 and 714. Preferably, an instrument or system is used by the practitioner to precisely form the geometric features 791 to the appropriate size, shape and depth. Once the geometric features 791 have been formed, the end locks 793 of each polymeric insert 792 are accommodated within opposing geometric features 791. Adhesive 34, shown in FIG. 2, may be applied to the surface of the polymeric insert 792 to secure it within the geometric feature 791. The mechanical joint formed by accommodating the polymeric insert 792 within the geometric feature 791 prevents separation of the first and second sternum portions 712 and 714.

Referring to FIG. 29, in another embodiment of the present invention, the structural members 890 spanning the incision 816 may include one or more polymeric biscuits 894. The polymeric biscuits 894 may be pressed into the cancellous bone 828 of sternum 810 to add support after closure. Preferably, the biscuits 894 are formed from a material that has osteoconductive properties to promote bone growth as the sternum 810 heals, and, even more preferably, the biscuits 894 are formed from substantially the same material as the adhesive 34, shown in FIG. 2. As discussed above, rather than being formed from biocompatible polymeric material, the structural members may instead be formed from allograft bone, metal or any other rigid implantable material.

During the sternal closure procedure, the biscuits 894 are partially pressed into the cancellous bone 828 of one of the sternum portions, for example, the second sternum portion 814. Preferably, the biscuits are pressed into the cancellous bone 828 so that approximately half of the biscuit is accommodated within the second sternum portion 814. The adhesive 34, shown in FIG. 2, may then be applied to the cut surfaces 824. The first and second sternum portions 812 and 814 may then be brought proximate to one another. As the first and second sternum portions 812 and 814 are brought proximate to one another, the biscuits 894 are pressed into the cancellous bone 828 of the other sternum portion, for example, the first sternum portion 812. Once the sternum 810 has been closed, the biscuits 894 provide structural support to the sternum 810 by spanning the incision 816. Additionally, adhesive 834 may be applied around the biscuit 894, prior to pressing the biscuit into the cancellous bone 828, to provide adhesive strength to the closed incision 816. The application of adhesive 834 around the biscuit 894 may be in addition to or instead of the application of adhesive 34, shown in FIG. 2, to the cut surfaces 824.

Figure 30:
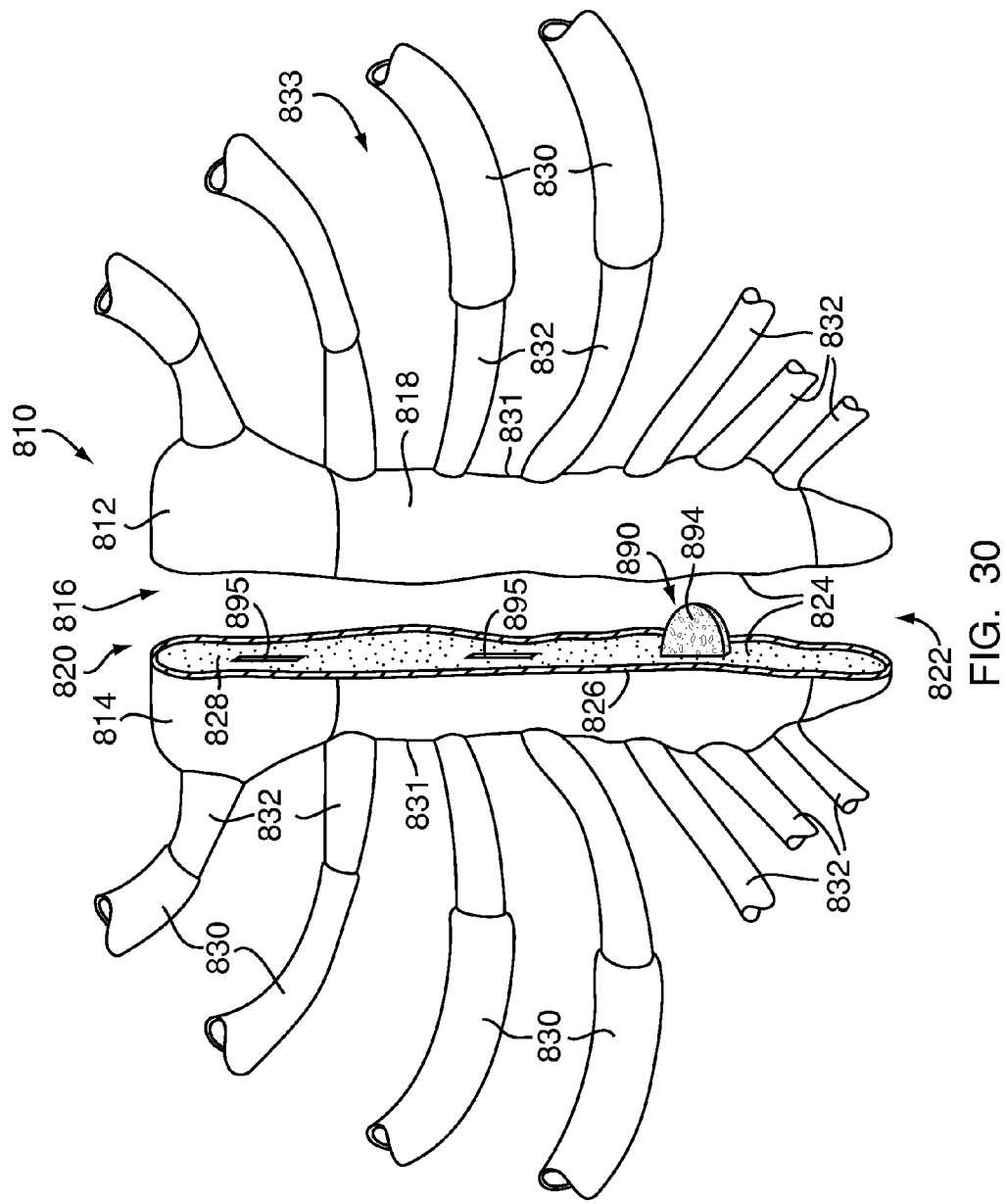
FIG. 30 is a perspective view of another embodiment for accommodating the structural member within the separated sternum of FIG. 29.

Referring to FIG. 30, rather than pressing the biscuits 894 into the cancellous bone 828, spacer accommodations 895 may be formed by cutting away portions of the cancellous bone 828 while the first and second sternum portions 812 and 814 are separated. The biscuits 894 may be coated with adhesive 834, shown in FIG. 29, if desired, and inserted into the spacer accommodations 895 of either the first sternum portion 812 or the second sternum portion 814. The remainder of each biscuit 894 is then inserted into the other of the first sternum portion 812 or the second sternum portion 814 when the first and second sternum portions 812 and 814 are brought proximate to one another. This embodiment may be particularly beneficial for patients with relatively rigid cancellous bone 828, where pressing the biscuit 894 into the cancellous bone 828 is impractical.

Figure 31:
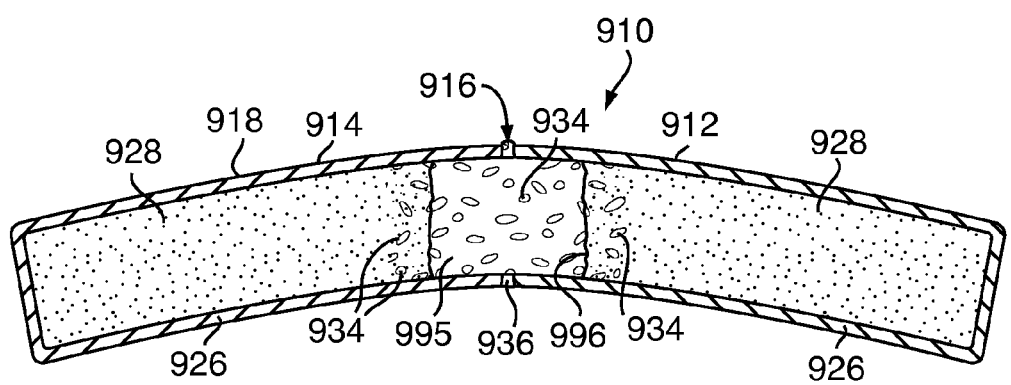
FIG. 31 is a cross-sectional view of another embodiment of the separated sternum with the structural member placed therein of FIG. 29.

Referring to FIG. 31, in another embodiment of the present invention, a putty-like material volume 996 may be inserted into spacer accommodations 995 of the first and second sternum portions 912 and 914, after which the putty-like material volume 996 cures to form the structural spacer spanning the incision 916. Preferably, the putty-like material volume 996 is formed from an osteoconductive material, and, even more preferably, from the same material as the adhesive 934. The space accommodations 995 are formed by cutting away portions of cancellous bone 928 while the first and second sternum portions 912 and 914 are separated. After the portions of cancellous bone 928 have been cut away from each of the first and second sternum portions 912 and 914 to form the spacer accommodations 995, the putty-like material volume 996 can then be shaped, if necessary, and inserted into the spacer accommodation 995 of either the first sternum portion 912 or the second sternum portion 914. The remainder of the putty-like material volume 996 is then inserted into the other of the first sternum portion 912 or the second sternum portion 914 when the first and second sternum portions 912 and 914 are brought proximate to one another. The putty-like material volume 996 then cures within the spacer accommodations 995 to add structural support to the closed sternum 910 by spanning the incision 916.

Figure 32:
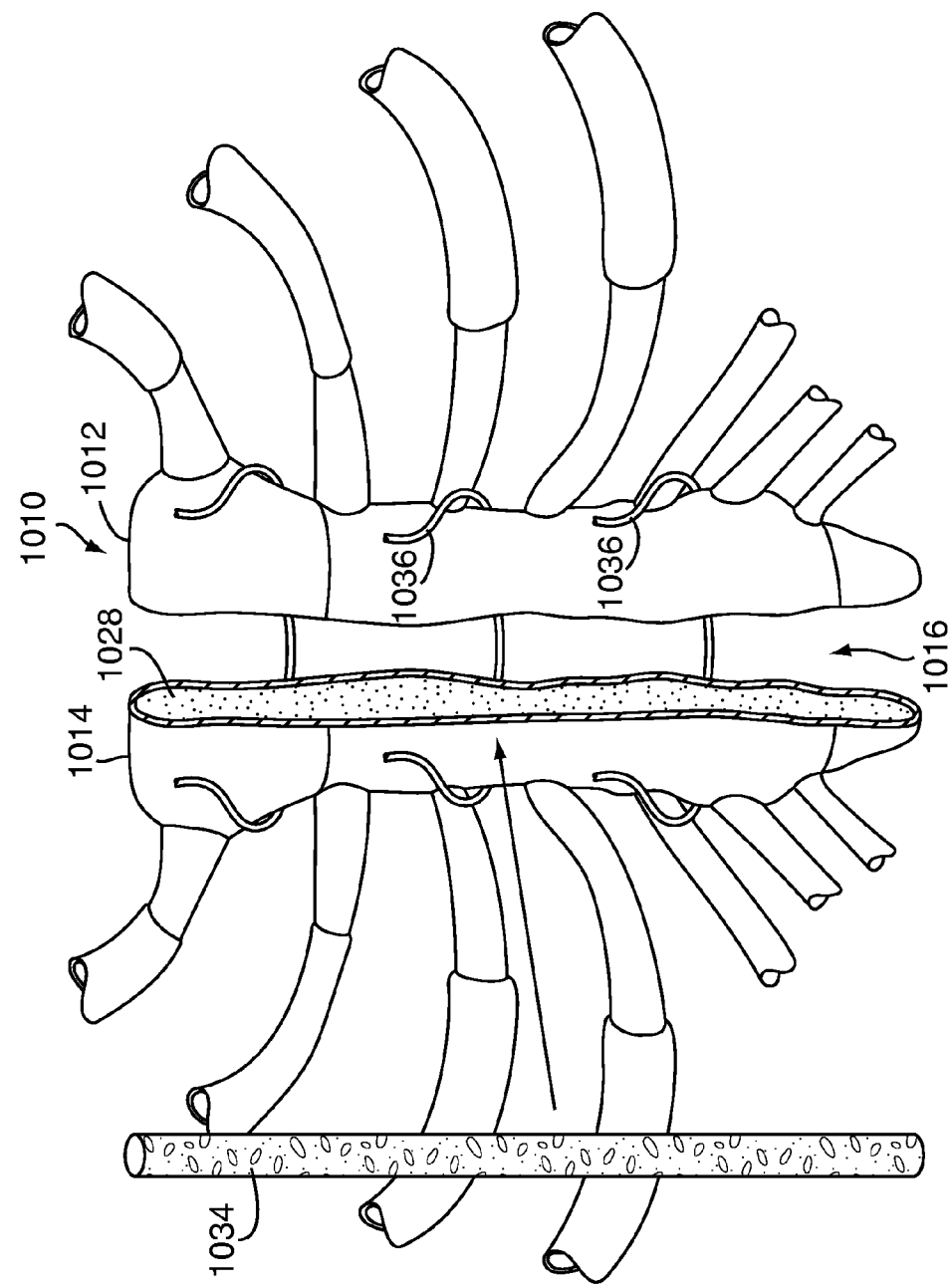
FIG. 32 is a perspective view of a separated sternum having adhesive placed therein according to another embodiment of the present invention.

Referring to FIG. 32, in some embodiments, the adhesive 1034 may be allowed to partially polymerize prior to application of the adhesive 1034 to the incision 1016. Preferably, the adhesive 1034 is allowed to polymerize to a point at which the adhesive 1034 is able to hold its own shape through cohesion. For example, the adhesive 1034 may be allowed to polymerize to the putty-like state discussed above before being applied to the incision 1016. Allowing the adhesive 1034 to partially polymerize improves handling by reducing tackiness of the adhesive 1034 and may allow the adhesive 1034 to be handled and/or applied to the incision 1016 without the use of application tools. The adhesive 1034 is preferably manipulated or shaped prior to insertion into the incision 1016 to achieve a desired shape, such as by molding, rolling, pulling, hand manipulation or the like. For example, in some embodiments, the adhesive 1034 may be rolled or pulled to form an elongated cylindrical or rope-like shape that is approximate in length to the length of the cancellous bone 1028. In other embodiments, the adhesive 1034 may be formed into multiple shorter strips that are applied in series along the length of the incision 1016.

In operation, the adhesive 1034 may be formed in substantially the same manner discussed above. If the adhesive 1034 is to be shaped by molding, the adhesive 1034 may then be poured or applied to the mold and allowed to cure to the partially polymerized putty-like state. In other embodiments, the adhesive 1034 may simple be allowed to partially polymerize in any suitable container and then removed and shaped once the partially polymerized putty-like state is achieved. If compressive devices 1036, such as wires, are used to secure the first and second sternum portions 1012 and 1014 together, they may be loosely positioned around the sternum 1010 prior formation of the adhesive 1034 or, more preferably, the compressive devices 1036 may be positioned while the adhesive 1034 is partially polymerizing. Once the partially polymerized adhesive 1034 has been shaped, it may be inserted into the incision 1016 and the incision 1016 may then immediately be closed by bringing the first and second sternum portions 1012 and 1014 together. Bringing the first and second sternum portions 1012 and 1014 together squishes the adhesive 1034 within the incision and into the cancellous bone 1028. If compressive devices 1036 are used, they may then be secured around the sternum 1010 to hold the first and second sternum portions 1012 and 1014 together. The adhesive 1034 will then finish polymerizing within the incision 1016 to provide the adhesive bond between the first and second sternum portions 1012 and 1014 in substantially the same manner as discussed above.

Although this method has been described with the adhesive 1034 being applied to the incision 1016 substantially immediately after shaping of the adhesive 1034, in some embodiments, polymerization of the adhesive 1034 may be substantially suspended while the adhesive 1034 is in the partially polymerized putty-like state for use in a future surgical procedure. For instance, polymerization of the adhesive 1034 may be suspended by lowering the temperature of the adhesive 1034. Then, when the temperature of the adhesive 1034 is increased in the future, polymerization of the adhesive 1034 will resume.

Figure 33:
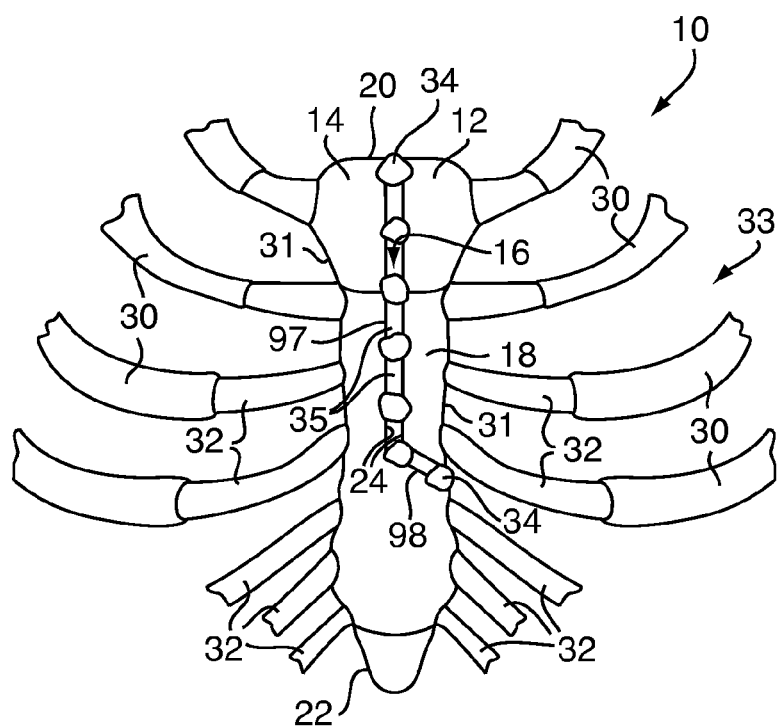
FIG. 33 is a front view of a sternum closed by adhesive after a partial sternotomy according to another embodiment of the present invention.

Although the methods for sternal closure of the present invention have thus far been described with regard to a median sternotomy, it should be understood by those skilled in the art that the present invention may also be used for other surgical procedures. For example, referring to FIG. 33, the methods according to the present invention may also close a sternum 10 after a partial sternotomy wherein the incision 16 includes a longitudinal portion 97 extending from the upper end 20 or lower end 22 of the sternum partway along the midline of the anterior surface 18 to a transverse incision portion 98, which extends to the peripheral edge 31, to separate the sternum 10 into first and second sternum portions 12 and 14. During the sternum closure procedure, adhesive 34 may be applied to the incision 16 in the same manner discussed above. Additionally, the adhesive 34 is preferably applied to both the transverse portion 98 and the longitudinal portion 97 of the incision 16 to provide enhanced stability by bonding the first and second sternum portions 12 and 14 in multiple directions.

Figure 34:
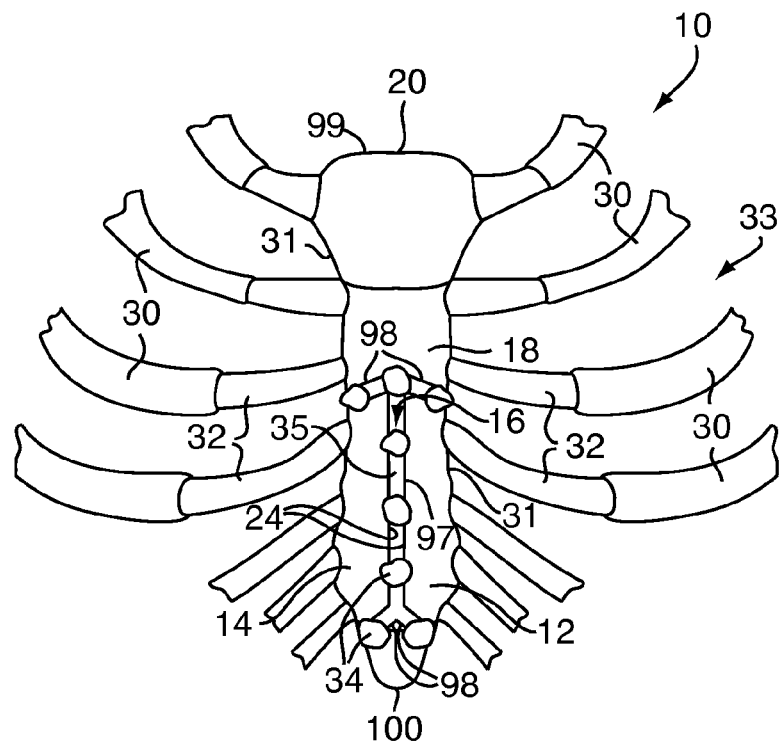
FIG. 34 is a front view of a sternum closed by adhesive after a hemi sternotomy according to another embodiment of the present invention.

Similarly, referring to FIG. 34, the methods of the present invention may also be used to close a sternum 10 after a hemi sternotomy, wherein the incision 16 includes longitudinal portion 97 extending through a central part of the sternum 10 along the midline of the anterior surface 18 with transverse incision portions 98 at the upper and lower ends of the longitudinal portion 97 to separate the sternum 10 into first and second sternum portions 12 and 14, as well as upper and lower sternum portions 99 and 100. During the sternum closure procedure, adhesive 34 may be applied to the incision 16 in the same manner discussed above and is preferably applied to both the transverse portions 98 and the longitudinal portion 97 to provide enhanced stability by bonding the first and second sternum portions 12 and 14 in multiple directions.

An advantage of the methods for sternal closure according to the present invention over the prior art is that the adhesive 34, 434, 534, 634, 834 and 934 resists sliding of one cut surface 24, 124, 624, 724 and 824 relative to the other, flexing motion of the first sternum portion 12, 112, 412, 512, 612, 712, 812 and 912 and/or the second sternum portion 14, 414, 514, 614,714, 814 and 914 about the cut surfaces 24, 124, 624, 724 and 824, as well as relative motion between the first sternum portion 12, 112, 412, 512, 612, 712, 812 and 912 and the second sternum portion 14, 414, 514, 614,714, 814 and 914 in the direction normal to the cut surfaces 24, 124, 624, 724 and 824. Thus, the present invention is able to reduce pain and discomfort experienced by patients due to all of these relative movements. Additionally, the present invention reduces the likelihood of other complications caused by relative motion of the first sternum portion 12, 112, 412, 512, 612, 712, 812 and 912 and second sternum portion 14, 414, 514, 614,714, 814 and 914, such as infections.

The present invention is also advantageous over the prior art because resisting the shearing and flexing relative movement of the first sternum portion 12, 112, 412, 512, 612, 712, 812 and 912 and the second sternum portion 14, 414, 514, 614,714, 814 and 914 reduces the buildup of soft fibrous scar tissue across the incision 16,416, 716, 816 and 916 at the surgical site, which may result in a non-union or dehiscence. Thus, further surgery to rejoin the first sternum portion 12, 112, 412, 512, 612, 712, 812 and 912 and the second sternum portion 14, 414, 514, 614,714, 814 and 914 may be avoided by the application of adhesive 34, 434, 534, 634, 834 and 934 according to the methods of the present invention.

Additionally, the present invention is advantageous over the prior art plate devices because the cured adhesive 34, 434, 534, 634, 834 and 934 can be cut in a similar manner to bone, i.e. with a sternal saw. Thus, if necessary, the present invention allows for future access to the thoracic cavity to be gained quickly using known techniques.

The present invention also advantageously provides various tools for preparing and cleaning the cut surfaces 24, 124, 624, 724 and 824 to reduce undesirable contamination of the adhesive 34, 434, 534, 634, 834 and 934 during polymerization. In some embodiments, the tools also advantageously protect sensitive organs from injury during the sternal closure procedure. Additionally, in some embodiments, the tools improve ease of application of the adhesive 34, 434, 534, 634, 834 and 934 to the cut surfaces 24, 124, 624, 724 and 824 when compared to conventional devices.

The present invention is also advantageous in that it can be implemented to resist the shearing and flexing relative movement of the first sternum portion 12, 112, 412, 512, 612, 712, 812 and 912 and the second sternum portion 14, 414, 514, 614,714, 814 and 914 while still being used with additional compressive devices 78, which provide compressive force for resisting separation of the first sternum portion 12, 112, 412, 512, 612, 712, 812 and 912 and the second sternum portion 14, 414, 514, 614,714, 814 and 914 in the direction normal to the cut surfaces 24, 124, 624, 724 and 824. Additionally, when used with compressive devices 78, the adhesive 34, 434, 534, 634, 834 and 934 of the present invention allows for fewer compressive devices 78 to be used when compared to prior art sternal closure devices. Thus, the risk of injury to the patient due to wires or cables being passed behind the sternum 10, 110, 410, 510, 610, 710, 810 and 910 and across surgical grafts is reduced.

Additionally, the present invention is advantageous over the prior art because it provides a method for inhibiting the compressive devices 78 from cutting into the sternum 10, 110, 410, 510, 610, 710, 810 and 910, which can lead to loosening of the compressive devices 78 and separation of the first sternal portion 12, 112, 412, 512, 612, 712, 812 and 912 and the second sternum portion 14, 414, 514, 614,714, 814 and 914 that can result in pain, delayed healing and/or additional surgical procedures.

Although this invention has been shown and described with respect to the detailed embodiments thereof, it will be understood by those skilled in the art that various changes in form and detail thereof may be made without departing from the spirit and the scope of the invention. For example, the geometric features 791 may be formed in a variety of shapes including rectangular and trapezoidal.

What is claimed is:

1. A method for closing a sternum separated into at least a first sternum portion having a first cut surface and a second sternum portion having a second cut surface, the method comprising:
   preparing at least one cut surface of at least one sternum portion to receive an adhesive;
   applying the adhesive to at least a portion of the least one cut surface;
   positioning the first cut surface proximate to the second cut surface; and
   allowing the adhesive to at least partially bond with the first cut surface and the second cut surface,
   wherein preparing the at least one cut surface includes applying a hemostatic chemical agent thereto.

2. The method according to claim 1, wherein the at least one cut surface is prepared by brushing.

3. The method according to claim 1, additionally comprising cleaning at least a portion of an anterior surface of the at least one sternum portion.

4. The method according to claim 3, wherein the cleaning of the portion of the anterior surface is substantially simultaneous with the preparing of the at least one cut surface.

5. The method according to claim 1, wherein the at least one cut surface is prepared by a lavage system, 6. The method according to claim 5, additionally comprising protecting sensitive organs from contact with pressurized cleaning fluid from the lavage system.

7. The method according to claim 6, wherein the protective organs are protected by a protective blade connected to a nozzle of the lavage system.

8. The method according to claim 5, additionally comprising vacuuming cleaning fluid and contaminants from the at least one cut surface.

9. The method according to claim 5, wherein the adhesive is applied to the cut surface through a nozzle of the lavage system.

10. A method for closing a sternum separated by an incision into at least a first sternum portion and a second sternum portion, the method comprising:
    bringing the first sternum portion and second sternum portion into contact at the incision;
    fastening the first sternum portion to the second sternumn portion with a compressive device: and
    introducing adhesive into the incision,
    wherein the step of introducing adhesive includes forming at least one hole in at least a portion of one sternal portion and introducing adhesive through the hole.

11. The method according to claim 10, additionally comprising the step of forming at least a second hole in at least a portion of one sternal portion and introducing a vacuum through the hole.

12. The method according to claim 10, additionally comprising the step of compressing cancellous bone of at least one sternum portion within the vicinity of the incision to form an adhesive receiving cavity.

13. The method according to claim 12, wherein a balloon is introduced to the cancellous bone of at least one sternum portion and is inflated to form the adhesive receiving cavity.

* * * * *